United States Patent [19]
Holt et al.

[11] Patent Number: 5,618,806
[45] Date of Patent: Apr. 8, 1997

[54] 17α AND 17β-SUBSTITUTED ESTRA-1,3,5(10)-TRIENE-3-CARBBOXLIC ACID

[75] Inventors: Dennis A. Holt, Stow, Mass.; Mark A. Levy, Wayne, Pa.

[73] Assignee: SmithKline Beecham Corporation

[21] Appl. No.: 325,462

[22] PCT Filed: Apr. 22, 1993

[86] PCT No.: PCT/US93/03778

§ 371 Date: Oct. 28, 1994

§ 102(e) Date: Oct. 28, 1994

[87] PCT Pub. No.: WO93/22333

PCT Pub. Date: Nov. 11, 1993

[30] Foreign Application Priority Data

Apr. 30, 1992 [GB] United Kingdom .................. 9209408
Nov. 18, 1992 [GB] United Kingdom .................. 9224210

[51] Int. Cl.⁶ .......................... A61K 31/56; C07J 75/00; C07J 9/00
[52] U.S. Cl. .................. 514/169; 514/171; 514/172; 514/174; 514/175; 514/176; 540/108; 540/110; 552/540; 552/546; 552/548; 552/552; 552/553; 552/554; 552/556; 552/558; 552/610; 552/611
[58] Field of Search ..................... 552/546, 552, 552/554, 556, 558, 611, 610, 540, 548, 553; 540/108, 110; 514/171, 174, 175, 176, 172, 169

[56] References Cited

U.S. PATENT DOCUMENTS

| 4,954,446 | 9/1990 | Holt et al. |
| 5,017,568 | 5/1991 | Holt et al. |
| 5,212,166 | 5/1993 | Panzerl et al. |

FOREIGN PATENT DOCUMENTS

| 0343954 | 11/1989 | European Pat. Off. |
| 0465123A2 | 1/1991 | European Pat. Off. |
| 0465142A1 | 1/1992 | European Pat. Off. |
| 0567271A2 | 10/1993 | European Pat. Off. |
| WO93/14107 | 7/1993 | WIPO |
| WO94/11385 | 5/1994 | WIPO |

*Primary Examiner*—Kimberly J. Prior
*Attorney, Agent, or Firm*—Wayne J. Dustman; Charles M. Kinzig; Edward T. Lentz

[57] ABSTRACT

Invented are 17α and 17β-substituted acyl-3-carboxy aromatic A ring analogues of steroidal synthetic compounds. Representative of such compounds include the following

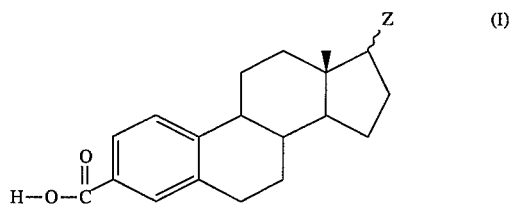

wherein Z is α or β

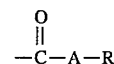

in which A is absent or present as a linear or branched, saturated or unsaturated hydrocarbon chain containing from 1–6 carbon atoms and R is a) a linear or branched, saturated or unsaturated hydrocarbon chain containing 1–12 carbon atoms substituted with one or more substituents selected from the group consisting of: —$OC_6$–$C_{12}$aryl, —$OC_1$–$C_4$alkyl, halogen, carboxy and —$S(O)_n R^7$, where n is 0–2 and $R^7$ is hydrogen or $C_{1-4}$alkyl;

b) $C_3$–$C_8$ nonaromatic, unsaturated or saturated, cycloalkyl, optionally substituted with one or more substituents selected from the group consisting of: —$OC_6$–$C_{12}$aryl, —$(CH_2)_m$OH, —$OC_1$–$C_4$alkyl, $C_6$–$C_{12}$aryl, $C_1$–$C_4$alkyl, trifluoromethyl, halogen, —$(CH_2)_p$COOH, —$S(O)_n R^7$ and protected —OH, where m is 0–4, p is 0–3, n is 0–2 and $R^7$ is hydrogen or $C_{1-4}$alkyl; or c) $C_4$–$C_{12}$aryl, optionally containing one or more heteroatoms, provided that when C is 4 the aromatic ring contains at least one heteroatom, and optionally substituted with one or more substituents selected from the group consisting of:
—$OC_6$–$C_{12}$aryl, —$(CH_2)_m$OH, $C_6$–$C_{12}$aryl, $C_1$–$C_4$alkyl, —$OC_1$–$C_4$alkyl, trifluoromethyl, halogen, —$(CH_2)_p$COOH, —$S(O)_n R^7$ and protected —OH, where m is 0–4, p is 0–3, n is 0–2 and $R^7$ is hydrogen or $C_{1-4}$alkyl. Also invented are pharmaceutical compositions containing these compounds, and methods for using these compounds to inhibit steroid 5α-reductase. Also invented are intermediates and processes used in preparing these compounds.

24 Claims, No Drawings

17α AND 17β-SUBSTITUTED ESTRA-1,3,5(10)-TRIENE-3-CARBBOXLIC ACID

This application is a 371 of application PCT/US93/03778 filed Apr. 22, 1993.

FIELD OF THE INVENTION

The present invention relates to certain novel 17α and 17β substituted acyl 3-carboxy aromatic A ting steroidal compounds, pharmaceutical compositions containing these compounds, and methods for using these compounds to inhibit steroid 5-α-reductase. Also invented are novel intermediates and processes useful in preparing these compounds.

DESCRIPTION OF RELATED ART

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective control results in excessive androgen hormone production. For example, acne vulgaris, seborrhea, female hirsutism, male pattern baldness and prostate diseases such as benign prostatic hypertropy are correlated with elevated androgen levels. Additionally, the reduction of androgen levels has been shown to have a therapeutic effect on prostate cancer.

Testosterone is the principal androgen secreted by the testes and is the primary androgenic steroid in the plasma of males. It now is known that 5-α-reduced androgens are the active hormones in some tissues such as the prostate and sebaceous gland. Circulating testosterone thus serves as a prohormone for dihydrotestosterone (DHT), its 5-α-reduced analogue, in these tissues but not in others such as muscle and testes. Steroid 5-α-reductase is a nicotinamide adenine dinucleotide phosphate (NADPH) dependent enzyme that converts testosterone to DHT. The importance of this enzyme in male development was dramatically underscored by the discovery of a genetic steroid 5-α-reductase deficiency in male pseudohermaphrodites. Imperato-McGinley, J., et al., (1979), *J. Steroid Biochem.* 11:637–648.

Recognition of the importance of elevated DHT levels in various disease states has stimulated many efforts to synthesize inhibitors of this enzyme. Among the most potent inhibitors identified to date are 3-carboxy-estra-1,3,5(10) triene steroidal derivatives.

A number of 5-α-reductase inhibiting compounds are known in the art. For example, 1. *J. Steroid Biochem.*, Vol. 34, Nos. 1–6 pp. 571–575(1989), by M. A. Levy, et al., describes the interaction mechanism between rat prostatic steroid 5-alpha reductase and 3-carboxy- 17β-substituted steroids;
2. *J. Med. Chem.* (1990) Vol. 33, pp. 937–942, by D. A. Holt, et al., describes the new steroid class of A ring aryl carboxylic acids;
3. *TIPS* (December 1989) Vol. 10, pp. 491–495, by B. W. Metcalf, et al., describes the effect of inhibitors of steroid 5α-reductase in benign prostatic hyperplasia, male pattern baldness and ache; and
4. *EPO Publn.* No. 0 343 954 A3, to D. A. Holt, et al., (SmithKline Beckmann) describes steroidal 3-carboxylic acid derivatives as useful 5-α-reductase inhibitors.

However, none of the above references specifically suggests that any of the novel steroidal 17α or 17β-substituted acyl 3-carboxy-estra 1,3,5(10) triene compounds of the present invention would have utility as potent testosterone 5-α-reductase inhibitors.

SUMMARY OF THE INVENTION

This invention relates to a compound of the formula I:

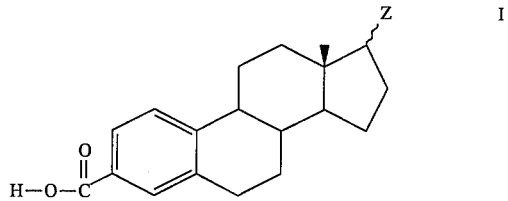

wherein Z is α or β

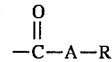

in which A is absent or present as a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting off aryloxy, alkoxy, acyloxy, amino, N-acylamino, nitro, cyano, oxo, halogen, —C(O)OR$^6$ and —S(O)$_n$R$^5$, where
R$^6$ is hydrogen or alkyl,
n is 0–2 and
R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of: alkoxy, acyloxy, amino, N-acylamino, oxo, hydroxy, cycloalkyl, substituted cycloalkyl, aryloxy, —C(O)OR$^6$, —S(O)$_n$R$^7$, nitro, cyano, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl;

b) cycloalkyl is nonaromatic, unsaturated or saturated, cyclic or polycyclic C$_3$–C$_{12}$, optionally containing one or more heteroatoms, and optionally substituted with one or more substituents selected from the group consisting off aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting off alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where
R$^6$ is hydrogen or alkyl,
n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, $C_6$–$C_{12}$aryl, substituted $C_6$–$C_{12}$aryl and protected —OH, where R$^6$ is hydrogen or alkyl, n is 0–2 and R$^7$ is hydrogen or alkyl; and c) aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where R$^6$ is hydrogen or alkyl, n is 0–2, R$^7$ is hydrogen or alkyl and R$^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where R$^6$ is hydrogen or alkyl, n is 0–2 and R$^7$ is hydrogen or alkyl; and pharmaceutically acceptable salts, hydrates, solvates and esters thereof.

The invention also is a method for inhibiting 5-α-reductase activity in mammals, including humans, that comprises administering to a subject an effective amount of a presently invented 5-α-reductase inhibiting compound. In a further aspect of the invention there are provided novel intermediates and novel processes useful in preparing the presently invented 5-α-reductase inhibiting compounds. Included in the present invention are pharmaceutical compositions comprising a pharmaceutical carrier and compounds useful in the methods of the invention. Also included in the present invention are methods of co-administering administering the presently invented 5-α-reductase inhibiting compounds with further active ingredients.

DETAILED DESCRIPTION OF THE INVENTION

The compounds of this invention that inhibit 5-α-reductase have the following Formula (I):

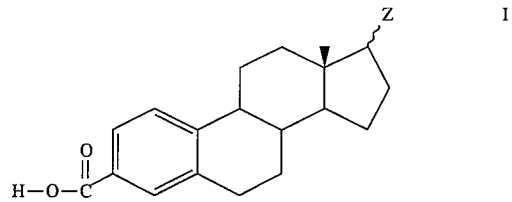

wherein Z is α or β

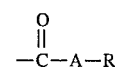

in which A is absent or present as a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$, where R$^6$ is hydrogen or alkyl, n is 0–2 and R$^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, amino, N-acylamino, oxo, hydroxy, cycloalkyl, substituted cycloalkyl, aryloxy, —C(O)OR$^6$, —S(O)$_n$R$^7$, nitro, cyano, halogen, $C_6$–$C_{12}$aryl, substituted $C_6$–$C_{12}$aryl and protected —OH, where R$^6$ is hydrogen or alkyl, n is 0–2 and R$^7$ is hydrogen or alkyl;

b) cycloalkyl is nonaromatic, unsaturated or saturated, cyclic or polycyclic $C_3$–$C_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where R$^6$ is hydrogen or alkyl, n is 0–2, R$^7$ is hydrogen or alkyl and R$^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and c) aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and pharmaceutically acceptable salts, hydrates, solvates and esters thereof.

Preferred among the presently invented compounds are those having the following Formula (II):

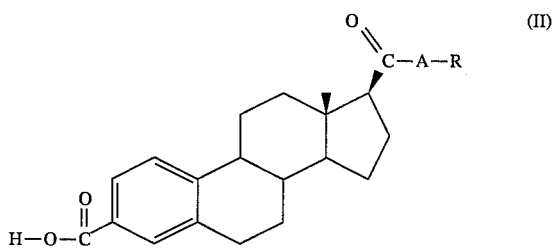

(II)

in which A is absent or present as a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of aryloxy, alkoxy, acyloxy, amino, N-acylamino, nitro, cyano, oxo, halogen, —C(O)OR$^6$ and —S(O)$_n$R$^5$, where $R^6$ is hydrogen or alkyl, n is 0–2 and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, amino, N-acylamino, oxo, hydroxy, cycloalkyl, substituted cycloalkyl, aryloxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl;

b) cycloalkyl is nonaromatic, unsaturated or saturated, cyclic or polycyclic $C_3$–$C_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting off alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and c) aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting off alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and pharmaceutically acceptable salts, hydrates, solvates and esters thereof.

Preferred among the presently invented Formula II compounds are those in which A is absent or present as a linear or branched, saturated or unsaturated hydrocarbon chain containing from 1–6 carbon atoms and R is a) a linear or branched, saturated or unsaturated hydrocarbon chain containing 1–12 carbon atoms substituted with one or more substituents selected from the group consisting of: —OC$_6$–C$_{12}$aryl, carboxy, —OC$_1$–C$_4$alkyl, halogen and —S(O)$_n$R$^7$, where n is 0–2 and R$^7$ is hydrogen or C$_{1-4}$alkyl;

b) C$_3$–C$_8$ nonaromatic, unsaturated or saturated, cycloalkyl, optionally substituted with one or more substituents selected from the group consisting off —OC$_6$–C$_{12}$aryl, —(CH$_2$)$_m$OH, —OC$_1$–C$_4$alkyl, C$_6$–C$_{12}$aryl, C$_1$–C$_4$alkyl, trifluoromethyl, halogen, —(CH$_2$)$_p$COOH, —S(O)$_n$R$^7$ and protected —OH, where m is 0–4, p is 0–3, n is 0–2 and R$^7$ is hydrogen or C$_{1-4}$alkyl; or c) C$_4$–C$_{12}$aryl, optionally containing one or more heteroatoms, provided that when C is 4 the aromatic ring contains at least one heteroatom, and optionally substituted with one or more substituents selected from the group consisting of: —OC$_6$–C$_{12}$aryl, —(CH$_2$)$_m$OH, C$_6$–C$_{12}$aryl, C$_1$–C$_4$alkyl, —OC$_1$–C$_4$alkyl, trifluoromethyl, halogen, —(CH$_2$)$_p$COOH, —S(O)$_n$R$^7$ and protected —OH, where m is 0–4, p is 0–3, n is 0–2 and R$^7$ is hydrogen or C$_{1-4}$alkyl; and pharmaceutically acceptable salts, hydrates, solvates and esters thereof.

Particularly preferred among Formula II compounds are those in which A is absent or present as a linear or branched, saturated or unsaturated hydrocarbon chain containing from 1–4 carbon atoms and R is a) C$_3$–C$_8$ nonaromatic, unsaturated or saturated cycloalkyl, optionally substituted with one or more substituents selected from the group consisting of: halogen, thio, methylsulfonyl, methylsulfoxyl, methylthio, carboxy, hydroxy, trifluoromethyl, phenoxy and methoxy or b) C$_4$–C$_{12}$aryl, optionally containing one more heteroatoms, provided that when C is 4 the aromatic ring contains at least one heteroatom, and optionally substituted with one or more substituents selected from the group consisting of: halogen, thio, methylsulfonyl, methylsulfoxyl, methylthio, carboxy, hydroxy, trifluoromethyl, phenoxy and methoxy and pharmaceutically acceptable salts, hydrates, solvates and esters thereof.

Particularly preferred among Formula II compounds are those in which A is absent or present as a linear or branched, saturated or unsaturated hydrocarbon chain containing from 1–4 carbon atoms and R is a) C$_5$–C$_7$ cycloalkyl or b) C$_4$–C$_{12}$ aryl, optionally containing one or more heteroatoms, provided that when C is 4 the aromatic ring contains at lease one heteroatom, and optionally substituted with one or more substituents selected from the group consisting off halogen, thio, methylsulfonyl, methylsulfoxyl, methylthio, carboxy, hydroxy, trifluoromethyl, phenoxy and methoxy and pharmaceutically acceptable salts, hydrates, solvates and esters thereof.

Particularly preferred among formula II compounds are:

17β-benzoyl-estra-1,3,5(10)-triene-3-carboxylic acid,
17β-(cyclohexylcarbonyl)-estra-1,3,5(10)-triene-3-carboxylic acid,
17β-(4-fluorobenzoyl)-estra-1,3,5(10)-triene-3-carboxylic acid,
17β-(benzylcarbonyl)-estra-1,3,5(10)-triene-3-carboxylic acid,
17β-(1-naphthylcarbonyl)-estra-1,3,5(10)-triene-3-carboxylic acid,
17β-(phenethylcarbonyl)-estra-1,3,5(10)-triene-3-carboxylic acid,
17β-(cyclohexylmethylcarbonyl)-estra-1,3,5(10)-triene-3-carboxylic acid,
17β-(cyclohexylethylcarbonyl)-estra-1,3,5(10)-triene-3-carboxylic acid,
17β-(4-biphenylcarbonyl)-estra-1,3,5(10)-triene-3-carboxylic acid,
17β-(3-phenylpropylcarbonyl)-estra-1,3,5(10)-triene-3-carboxylic acid,
17β-(4-methoxybenzoyl)-estra-1,3,5(10)-triene-3-carboxylic acid,
17β-(4-phenoxybenzoyl)-estra-1,3,5(10)-triene-3-carboxylic acid,
17β-(4-trifluoromethylbenzoyl)-estra-1,3,5(10)-triene-3-carboxylic acid,
17β-(4-methylsulfonylbenzoyl)-estra-1,3,5(10)-triene-3-carboxylic acid,
17β-(4-methylthiobenzoyl)-estra-1,3,5(10)-triene-3-carboxylic acid,
17β-(3,5-difluorobenzoyl)-estra-1,3,5(10)-triene-3-carboxylic acid,
17β-(phenylacetylenecarbonyl)-estra-1,3,5(10)-triene-3-carboxylic acid,
17β-(4-methoxyphenethylcarbonyl)-estra-1,3,5(10)-triene-3-carboxylic acid,
17β-(3,4-methylenedioxybenzoyl)-estra-1,3,5(10)-triene-3-carboxylic acid,
17β-(4-hydroxyphenethylcarbonyl)-estra-1,3,5(10)-triene-3-carboxylic acid,
17β-(4-carboxyphenethylcarbonyl)-estra-1,3,5(10)-triene-3-carboxylic acid,
17β-(E-cinnamoyl)-estra-1,3,5(10)-triene-3-carboxylic acid,
17β-(2-furanylcarbonyl)-estra-1,3,5(10)-triene-3-carboxylic acid,
17β-(4-fluorophenethylcarbonyl)-estra-1,3,5(10)-triene-3-carboxylic acid,
17β-(4-methylthiophenethylcarbonyl)-estra-1,3,5(10)-triene-3-carboxylic acid,
17β-(4-methylsulfoxylphenethylcarbonyl)-estra-1,3,5(10)-triene-3-carboxylic acid,
17β-(4-methylsulfonylphenethylcarbonyl)-estra-1,3,5(10)-triene-3-carboxylic acid,
17β-(2-thiophenylcarbonyl)-estra-1,3,5(10)-triene-3-carboxylic acid,
17β-(3-pyridylcarbonyl)-estra-1,3,5(10)-triene-3-carboxylic acid,
17β-(3-pyridylmethylcarbonyl)-estra-1,3,5(10)-triene-3-carboxylic acid,
17β-(4-pyridylmethylcarbonyl)-estra-1,3,5(10)-triene-3-carboxylic acid and
17β-(2-pyridylethylcarbonyl)-estra-1,3,5(10)-triene-3-carboxylic acid and pharmaceutically acceptable salts, hydrates, solvates and esters thereof.

The term "α", as used herein, follows standard chemical terminology and means down or that the corresponding substituent is attached below the plane of the paper.

The term "β", as used herein, follows standard chemical terminology and means up or that the corresponding substituent is attached above the plane of the paper.

By the term "protected hydroxy" or "protected —OH" as used herein, is meant the alcoholic or carboxylic-OH groups which can be protected by conventional blocking groups in the art as described in "Protective Groups In Organic Synthesis" by Theodora W. Greene, Wiley-Interscience, 1981, New York. Preferred are the triorganosilyl groups, e.g. t-butyldimethylsilyl, phenyldimethylsilyl, diphenylmethylsilyl, and the like.

As used herein C$_x$–C$_y$ is meant a moiety having from x to y carbons.

By the term "aryl" as used herein, unless otherwise defined, is meant cyclic or polycyclic aromatic $C_3$-$C_{12}$, optionally containing one or more heteroatoms, provided that when C is 3 the aromatic ring contains at least two heteroatoms and when C is 4 the aromatic ring contains at least one heteroatom, and optionally substituted with one or more substituents selected from the group consisting of: alkyl, $C_6$-$C_{12}$ aryl, substituted cycloalkyl, substituted $C_6$-$C_{12}$aryl, aryloxy, hydroxy, alkoxy, cycloalkyl, acyloxy, amino, N-acylamino, nitro, cyano, halogen, —C(O)OR$^6$, —S(O)$_n$R$^5$, protected —OH and alkyl substituted with one or more substituents selected from the group consisting of: alkoxy, acyloxy, $C_6$-$C_{12}$aryl, substituted $C_6$-$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen, and protected —OH, where R$^6$ is hydrogen or alkyl, n is 0–2, R$^7$ is hydrogen or alkyl and R$^5$ is hydrogen, cycloalkyl, $C_6$-$C_{12}$aryl, substituted cycloalkyl, substituted $C_6$-$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$-$C_{12}$aryl, substituted $C_6$-$C_{12}$aryl and protected —OH, where R$^6$ is hydrogen or alkyl, n is 0–2 and R$^7$ is hydrogen or alkyl.

Examples of aryl and substituted aryl substituents as used herein include: phenyl, naphthyl, furanyl, biphenyl, hydroxyphenyl, pyridyl, fluorophenyl, dihydroxyphenyl, methylenedioxyphenyl, dimethylhydroxyphenyl, methoxyphenyl, trifluoromethylphenyl carboxymethylphenyl, phenoxyphenyl, methylsulfonylphenyl, methylthiophenyl, difluorophenyl, carboxyphenyl, methylsulfoxylphenyl and thiophenyl.

Preferred examples of aryl and substituted aryl substituents as used herein include: phenyl, 4-fluorophenyl, 1-naphthyl, 4-biphenyl, 4-methoxyphenyl, 4-phenoxyphenyl, 4-trifluoromethylphenyl, 4-methylsulfonylphenyl, 4-methylthiophenyl, 3,5-difluorophenyl, 4-hydroxyphenyl, 4-carboxyphenyl, 2-furanyl, 4-methylsulfoxylphenyl, 3-thiophenyl, 2-pyridyl, 3-pyridyl, 4-pyridyl and 3,4-methylenedioxyphenyl.

By the term "$C_6$-$C_{12}$ aryl" as used herein, unless otherwise defined, is meant phenyl, naphthyl, 3,4-methylenedioxyphenyl, pyridyl, or biphenyl.

By the term "substituted" as used herein, unless otherwise defined, is meant that the subject chemical moiety has one or more substituents selected from the group consisting of: hydroxyalkyl, alkoxy, acyloxy, alkyl, amino, N-acylamino, hydroxy, —(CH$_2$)$_g$C(O)OR$^6$, —S(O)$_n$R$^7$, nitro, cyano, halogen, trifluoromethyl and protected —OH, where g is 0–6, R$^6$ is hydrogen or alkyl, n is 0–2, and R$^7$ is hydrogen or alkyl.

By the term "alkoxy" as used herein is meant —Oalkyl where alkyl is as described herein including —OCH$_3$ and —OC(CH$_3$)$_2$CH$_3$.

The term "cycloalkyl" as used herein unless otherwise defined, is meant a nonaromatic, unsaturated or saturated, cyclic or polycyclic $C_3$-$C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl and cyclopentyl.

By the term "acyloxy" as used herein is meant —OC(O)alkyl where alkyl is as described herein. Examples of acyloxy substituents as used herein include: —OC(O)CH$_3$, —OC(O)CH(CH$_3$)$_2$ and —OC(O)(CH$_2$)$_3$CH$_3$.

By the term "N-acylamino" as used herein is meant —N(H)C(O)alkyl, where alkyl is as described herein. Examples of N-acylamino substituents as used herein include: —N(H)C(O)CH$_3$, —N(H)C(O)CH(CH$_3$)$_2$ and —N(H)C(O)(CH$_2$)$_3$CH$_3$.

By the term "aryloxy" as used herein is meant —OC$_6$-C$_{12}$aryl where C$_6$-C$_{12}$aryl is phenyl, naphthyl, 3,4-methylenedioxyphenyl, pyridyl or biphenyl optionally substituted with one or more substituents selected from the group consisting of: alkyl, hydroxyalkyl, alkoxy, trifluoromethyl, acyloxy, amino, N-acylamino, hydroxy, —(CH$_2$)$_g$C(O)OR$^6$, —S(O)$_n$R$^7$, nitro, cyano, halogen and protected —OH, where g is 0–6, R$^6$ is hydrogen or alkyl, n is 0–2 and R$^7$ is hydrogen or alkyl. Examples of aryloxy substituents as used herein include:

phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain having $C_1$-$C_{12}$ carbon atoms. Examples of alkyl substituents as used herein include: —CH$_3$, —CH$_2$-CH$_3$, —CH$_2$-CH$_2$-CH$_3$, —CH(CH$_3$)$_2$, —C(CH$_3$)$_3$, —(CH$_2$)$_3$—(CH$_3$), —CH$_2$—CH(CH$_3$)$_2$ and —CH(CH$_3$)—CH$_2$-CH$_3$, —CH═CH$_2$.

By the term "treating" and derivatives thereof as used herein, is meant prophylatic or therapeutic therapy.

By the term "metal-catalyzed coupling reaction" as used herein is meant that the prepared 3-trifluoromethyl sulfonylate or 3-fluorosulfonylate compound is reacted in a suitable organic solvent, preferably toluene, dimethylformamide or THF with a base, preferably a tertiaryamine base such as triethylamine, pyridine or tributylamine, a phosphine such as bis(diphenylphosphino)alkane, preferably 1,3 bis(diphenylphosphino)propane or tri-o-tolyphosphine, or a $C_{1-6}$alkOH, and a metal catalyst, preferably a palladium catalyst such as palladium (II) acetate, palladium (II) chloride and bis(triphenylphosphine) palladium II acetate, and a coupling reagent.

By the term "coupling reagent" as used herein is meant a compound which is capable of reacting with an aryl radical to form a carboxylic add substituent. Carbon monoxide is a preferred coupling reagent which when added to the metal-catalyzed coupling reaction, as described herein, yields the desired carboxylic acid group.

Compounds of Formula (I) and compounds of Formula (V) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

The term "a-receptor antagonist", as used herein, refers to a known class of alpha-andrenergic receptor antagonist comounds, such as described in Lafferty, et al. U.S. Pat. No. 4,963,547, which are utilized in treating vascular disorders such as diabetes, cardiovascular disease, benign prostatic hypertrophy and ocular hypertension.

Preferred alpha-andrenergic receptor antagonists for use in the compositions and methods of the invention include amsulosin, terazosin, doxazosin, alfuzosin, indoramin, prazosin and 7-chloro-2-ethyl-3,4,5,6-tetrahydro-4- methylthieno[4,3,2-ef][3]-benzazepine.

By the term "amsulosin" as used herein is meant a compound of the structure

CH₃O—⟨ ⟩—CH₂—C(CH₃)(H)—NHCH₂CH₂O—⟨ ⟩—OCH₂CH₃
       |
     H₂NO₂S and salts, hydrates and solvates thereof.

Chemically, amsulosin is designated as (−)-(R)-5-[2-[[2-(Oethoxyphenoxy)ethyl]amino]propyl]-2-methoxybenzenesulfonamide.

Amsulosin is disclosed in U.S. Pat. No. 4,703,063 and claimed in U.S. Pat. No. 4,987,125 as being useful in treating lower urinary tract dysfunction.

By the term "terazosin" as used herein is meant a compound of the structure and salts, hydrates and solvates thereof.

Chemically, terazosin is designated as 1-(4-amino-6,7-dimethoxy-2 quinazolinyl)-4-[(tetrahydro-2-furoyl)carbonyl]piperazine. Terazosin is disclosed in U.S. Pat. No. 4,25 1,532.

By the term doxazosin as used herein is meant a compound of the structure and salts, hydrates and solvates thereof.

Chemically "doxazosin" is designated as 1-(4-amino-6,7dimethoxy-2-quinazolinyl)-4-[(2,3-dihydro-1,4-benzodioxin-2-yl)carbonyl]-piperazine.

Doxazosin is disclosed in U.S. Pat. No. 4,188,390.

By the term "alfuzosin" is meant a compound of the structure and salts, hydrates and solvates thereof.

Chemically alfuzosin is designated as N-[3-[(4-amino-6,7-dimethoxy-2-quinazolinyl)methylamino]propyl]tetrahydro-2-furancarboxamide.

Alfuzosin is disclosed in U.S. Pat. No. 4,315,007.

By the term "indoramin" as used herein is meant a compound of the structure and salts, hydrates and solvates thereof.

Chemically indoramin as designated N-[[1-[2-(1H-indol-3-yl)ethyl]-4-piperidinyl]benzamine.

Indoramin is disclosed in U.S. Pat. No. 3,527,761.

By the term "prazosin" as used herein is meant a compound of the structure and salt, hydrates and solvates thereof.

Chemically prazosin is designated as 1-(4-amino-6,7-dimethoxy-2-quinazolinyl)-4-(2-furanylcarbonyl)piperazine.

Prazosin is disclosed in U.S. Pat. No. 3,511,836.

"7-chloro-2-ethyl-3,4,5,6-tetrahydro-4-methylthieno[4,3,2-ef]-[3]benzazepine" as used herein is meant a compound of the structure and salts, hydrates and solvates thereof.

7-chloro-2-ethyl-3,4,5,6-tetrahydro-4-methylthieno[4,3,2-ef]-[3]benzazepine is disclosed in U.S. Pat. No. 5,006,52. Additionally all compounds disclosed in U.S. Pat. No. 5,006,521 as alpha-adrenergic receptor antagonist are preferred alpha-adrenergic receptor antagonist as used herein.

Persons skilled in the art can readily determine if a compound other than one specifically referred to herein is a alpha-andrenergic receptor antagonist by utilizing the assay described in Lafferty I. Thus, all such compounds are included within the scope of the term "alpha-andrenergic receptor antagonist" as used herein.

By the term "minoxidil" as used herein is meant the compound of the structure:

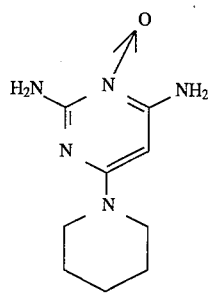

chemically minoxidil is designated as 2,4-pyrimidineadiamine, 6-(1-piperidinyl)-,3-oxide. Minoxidil is the active ingredient in Rogaine® which is sold as topical solution for stimulating hair growth by the Upjohn Company, Kalamazoo, Mich.

The term "aromatase inhibitor", as used herein, refers to a known class of compounds, steroidal and non-steroidal, which prevent the conversion of androgens to estrogens, such as described in Gormley et al. International Publication Number WO 92/18132. Aromatase inhibitors are disclosed in Gormley et al. as having utility in treating benign prostatic hyperplasia when used in combination with a 5-α-reductase inhibitor.

A preferred aromatase inhibitor for use in the compositions and methods of the invention 4-(5,6,7,8-tetrahydroimidazo-[1,5-α]pyridin-5-yl)benzonitrile (fadrazole). Fadrazole is disclosed in U.S. Pat. No. 4,728,645. Additionally, all compounds disclosed in Gormley, et al. International Publication No. WO 92/18132 as having aromatase inhibiting activity are preferred aromatase inhibitors as used herein.

As used herein, when a 5-α-reductase inhibitor, as described herein and a further active ingredient or ingredients are utilized together, said 5-α-reductase inhibitor can be co-administered with said further active ingredient or ingredients.

By the term "co-administering" and derivatives thereof as used herein is meant either simultaneous administration or any manner of separate sequential administration of a 5-α-reductase inhibiting compound, as described herein, and a further active ingredient or ingredients, such as other compounds known to treat the disease states of acne vulgaris, seborrhea, female hirsutism, male pattern baldness, benign prostate hypertrophy or prostatic adenocarcinoma or compounds known to have utility when used in combination with 5-α-reductase inhibitors. Preferably, if the administration is not simultaneous, the compounds are administered in a close time proximity to each other. Furthermore, it does not matter if the compounds are administered in the same dosage form, e.g. one compound may be administered topically and another compound may be administered orally.

Formula (II) compounds are prepared as shown in Schemes I through IV wherein A is as described in Formula (II). As used herein R⁸ is R or moieties which can be converted to those of R by chemical reactions readily is known to those of skill in the art, such as described in Derek Barton and U. D. Ollis, *Comprehensive Organic Chemistry: The Synthesis and Reactions of Organic Compounds*, Pub: Pergamon Press (1979), provided that $R^8$ does not include any such moieties that render inoperative the Schemes I through IV processes. As demonstrated in the following Examples, reactions to convert $R^8$ to R are performed on products of the synthetic pathways of Schemes I through IV or where appropriate or preferable, on certain intermediates in these synthetic pathways. For example, methylthio substituents can be converted to the methylsulfonyl by oxidation. Methoxy substituents can be converted to the hydroxy by treatment with boron tribromide. Hydroxy substituents can be converted to the carboxy by reaction with a trihaloalkylsulfonic anhydride, such as trifluoromethanesulfonic anhydride, followed by a metal catalyzed coupling reaction.

The novel compounds of Formula (II) of the present invention can be prepared by methods outlined in schemes 1–4 below and in the Examples from known and readily available estrone which has the formula:

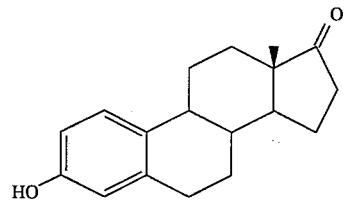

or from the 17β-carboxylic acid analogue of estrone, which is known and readily available.

Scheme I

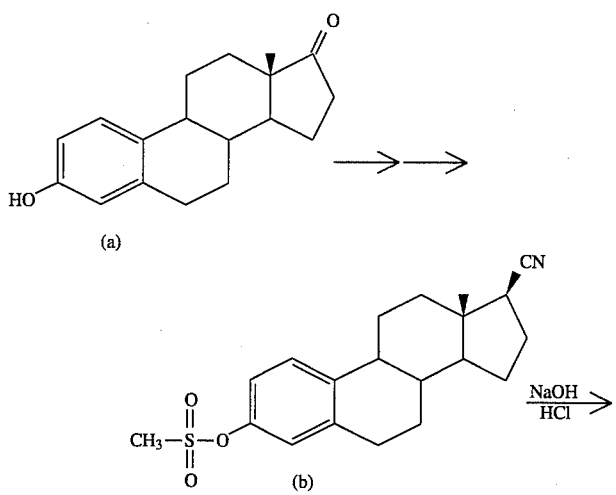

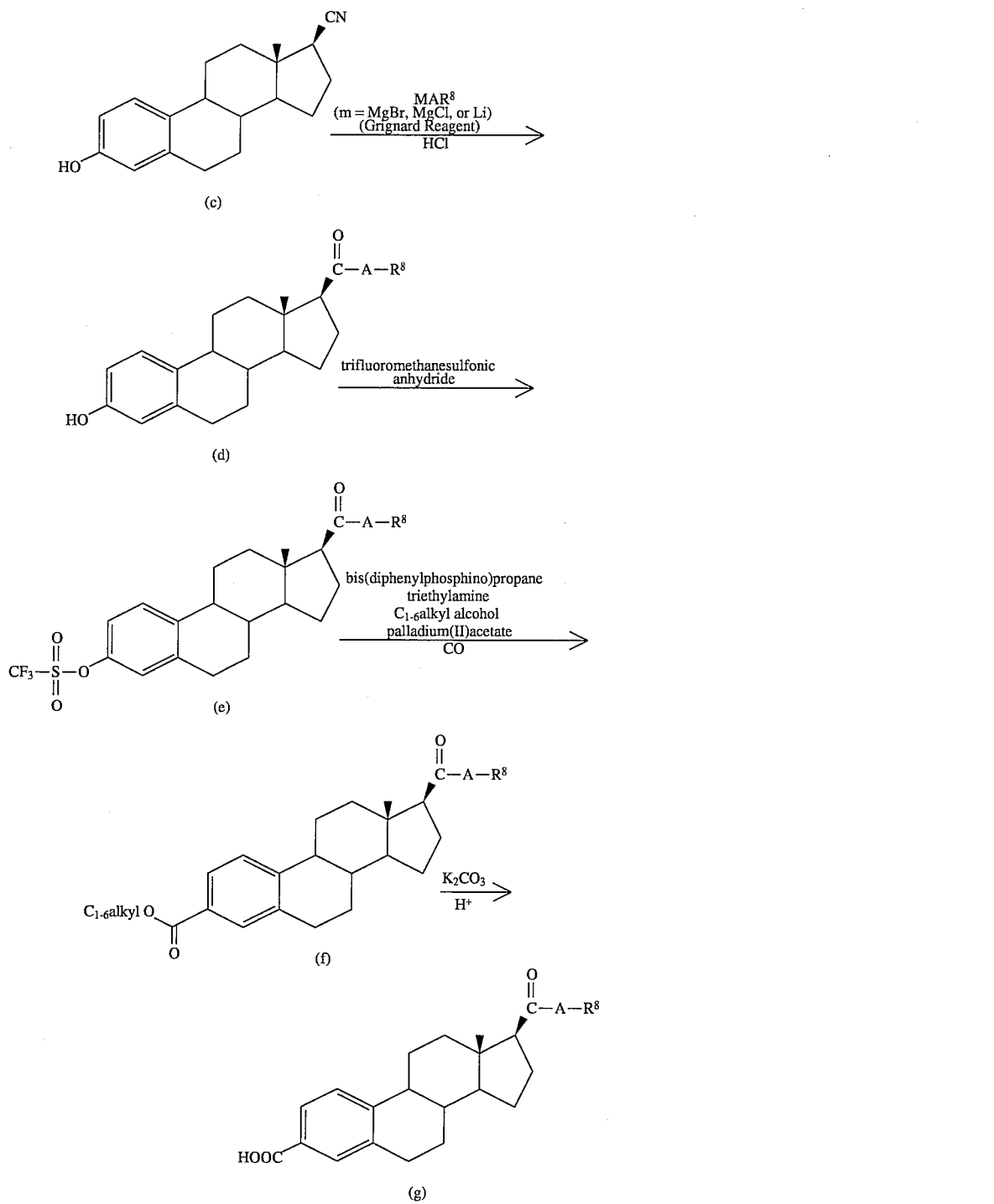

Scheme I outlines formation of Formula II compounds. As used scheme I compound (b) is prepared from compound (a) according to the procedure of Baldwin, et al., J. Chem. Soc. (c), 1.968, 2283–2289.

Compound (b) is then stirred in an appropriate organic solvent, preferably methanol, with a base, preferably sodium hydroxide, and then acidified to yield compound (c). Compound (c) is next treated with a Grignard reagent, described hereinbelow, in an appropriate organic solvent, preferably tetrahydrofuran or diethylether solvent, preferably at reflux temperature to yield formula (d) compounds.

A formula (d) compound and a base, preferably 2,5-di-t-butyl-3-methyl-pyridine in an appropriate organic solvent, preferably dichloromethane, is cooled to −20° C. to 20° C., preferably 0° C., and reacted with a trihaloalkyl sulfonic anhydride, preferably trifluoromethanesulfonic anhydride to form compounds (e).

Formula (f) compounds are prepared by reacting a formula (e) compound in a metal catalyzed coupling reaction. Preferably a formula (e) compound dissolved in dimethylformide (DMF) an organic base preferably, triethylamine, a phosphine, preferably bis(diphenylphosphino)propane, a palladium(II) compound, preferably, palladium(II) acetate, and a $C_{1-6}$alkyl alcohol ($C_{1-6}$alkOH), followed by addition of carbon monoxide (CO). Compounds (f) next are reacted with a suitable base, preferably potassium carbonate, and acidified to yield compounds (g).

SCHEME II

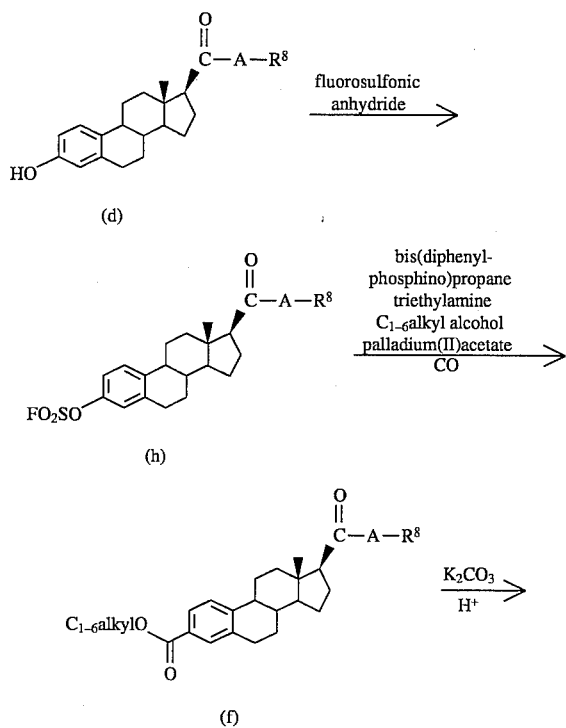

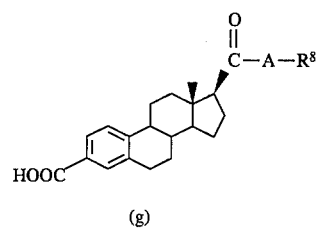

Scheme II outlines formation of Formula II compounds. The starting materials in Scheme II are formula (d) compounds prepared as described in Scheme I.

As used in Scheme II, a formula (d) compound and a base, preferably 2,5-di-t-butyl-3-methyl-pyridine in an appropriate organic solvent, preferably dichloromethane, is cooled to −20° C. to 20° C., preferably 0°, and reacted with fluorosulfonic anhydride to form compounds (h). Formula (f) compounds are prepared by reacting a Formula (h) compound in a metal-catalyzed coupling reaction. Preferably a Formula (h) compound is dissolved in dimethylformide (DMF) an organic base preferably triethylamine, a phosphine preferably bis (diphenylphospine)propane, a palladium(II) compound, preferably, palladium(II) acetate, and a $C_{1-6}$alkyl alcohol ($C_{1-6}$alkOH), followed by addition of carbon monoxide (CO). Compounds (f) next are reacted with a suitable base, preferably potassium carbonate, and acidified to yield compounds (g).

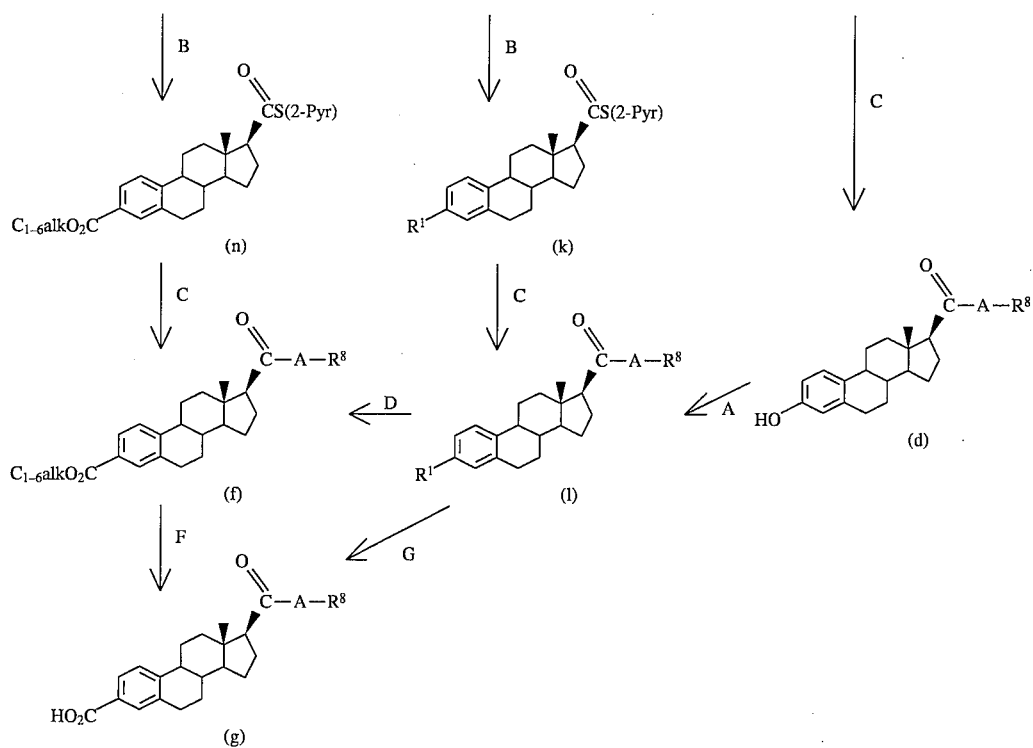

Scheme III outlines formation of Formula II compounds. As used in Scheme III A and $R^8$ are as described in Formula IV $R^1$ is $CF_3O_2SO-$ or $FO_2SO-$. As used in scheme III in the alkylation process (step C), the pyridylthio ester is reacted with an Li-$AR^8$ or an XMgA$R^8$ (X=Cl, Br) Grignard reagent (as described hereinbelow), preferably cyclohexylmagnesium chloride, 4-fluorophenylmagnesium bromide, phenylmagnesium bromide, phenethylmagnesium bromide, 1-naphthylmagnesium bromide, 4-biphenylmagnesium bromide cyclohexylmethylmagnesium bromide, cyclohexylethylmagnesium bromide, benzylmagnesium chloride, 3-phenylpropylmagnesium bromide, 4-methoxyphenylmagnesium bromide, 4-phenoxyphenylmagnesium bromide, 4-trifluoromethylphenylmagnesium bromide, 4-methylthiophenylmagnesium bromide, or 4-methoxyphenethylmagnesium bromide preferably in tetrahydrofuran to form the desired product, preferably 17β-cyclohexylcarbonyl-estra-1,3,5(10)-triene-3-carboxylic acid, 17β-(4-fluorobenzoyl)-estra-1,3,5(10)-triene-3-carboxylic acid, 17β-benzoyl-estra-1,3,5(10)-triene-3-carboxylic acid, 17β-(phenethylcarbonyl)-estra-1,3,5(10)-triene-3-carboxylic acid, 17β-(1-naphthylcarbonyl)-estra-1,3,5(10)-triene-3-carboxylic add, 17β-(4-biphenylcarbonyl)-estra-1,3,5(10)-triene-3-carboxylic acid, 17β-(cyclohexylethylcarbonyl)-estra-1,3,5(10)-triene-3-carboxylic acid, 17β-(cyclohexylmethylcarbonyl)-estra-1,3,5(10)-triene-carboxylic acid, 17β-(benzylcarbonyl)-estra-1,3,5(10)-triene-3-carboxylic acid, 17β-(3-phenylpropylcarbonyl)-estra-1,3,5(10)-triene-3-carboxylic acid, 17β-(4-methoxybenzoyl)-estra-1,3,5(10)-triene-3-carboxylic acid, 17β-(4-phenoxybenzoyl)-estra-1,3,5(10)-triene-3-carboxylic acid, 17β-(4-trifluoromethylbenzoyl)-estra-1,3,5(10)-triene-3-carboxylic acid, 17β-(4-methylthiobenzoyl)-estra-1,3,5(10)-triene-3-carboxylic acid, or 17β-(4-methoxyphenethylcarbonyl)-estra-1,3,5(10)-triene-3-carboxylic acid respectively, in one or two steps.

In Route 1, the 3-hydroxyl acid (i) is converted to the 3-trifluoromethylsulfonylate or 3-fluorosulfonylate derivative (j) (step A) by treating (i) with trifluoromethylsulfonyl anhydride or fluorosulfonic anhydride and an amine base, such as pyridine, preferably 2,5 di-t-butyl-3-methyl-pyridine, in an appropriate organic solvent, preferably dichloromethane at about −20° C. to 20° C., preferably 0°.

The activated ester (k) is produced (step B) by treating (j) with 2,2-dithiopyridyl and triphenylphosphine in an appropriate organic solvent solution preferably, tetrahydrofuran/toluene at room temperature for about 8–14 hours.

The 17-acyl derivative (1) is produced (step C) by treating (k) with a Grignard reagent, described hereinbelow, in tetrahydrofuran or diethyl ether solvent, at a temperature of about −50° to −70° C., for 1–16 hours.

The 3-alkyl ester (f) is produced (step D) by treating (1) under carbonylation conditions, preferably by bubbling carbon monoxide gas through a solution of (l) in an appropriate organic solvent, preferably methanol, containing palladium acetate catalyst, triphenylphosphine, and a tertiary organic amine preferably triethylamine at about room temperature for 1–16 hours. Compound (f) next are reacted with a suitable base, preferably potassium carbonate and acidified to yield compounds (g).

Compounds (g) can also be produced (step G) by treating (l) under carboxylation conditions, preferably by bubbling carbon monoxide gas through a solution of (l) in an appropriate non-alcoholic solvent, preferably DMSO, containing a palladium catalyst, preferably palladium (II) diacetate and 1,1-Bis(diphenylphosphino)ferrocene (DPPF); and a base, preferably potassium acetate, preferably at increased temperatures.

Note that, if used herein, if $R^8$ is aroyl, which also contains a protected hydroxy group, e.g. with dimethyl-t-butyl-silyl, this may be removed by treating with tetrabutylammonium floride in an appropriate, organic solvent, preferably tetrahydrofuran with a small amount of added acetic acid, from 0° C. to reflux for 1–4 hours prior to carrying out, for example, step F.

Route 2 involves converting the starting steroidal acid (i) to the 3-trifluoromethylsulfonylate or the 3-fluorosulfonylate derivative (j) by the above-described step A; carbonylating (j) to (m) by step D; forming the activated 2-pyridylthio ester (n) by step B; forming the 17-acyl compound (f) by step C; and hydrolyzing the 3-ester to the 3 acid final product (g) by step F.

Route 3 involves converting the starting acid (i) to the activated ester (o) by the above-described step B; forming the 17-acyl compound (d) by reacting (o) by the above described step C; converting (d) to the 3-trifluoromethylsulfonylate or 3-fluorosulfonylate derivative (l) by the above-described step A; and converting (l) to the final product (g) by the above described step G or by the above-described step D followed by the above described step F.

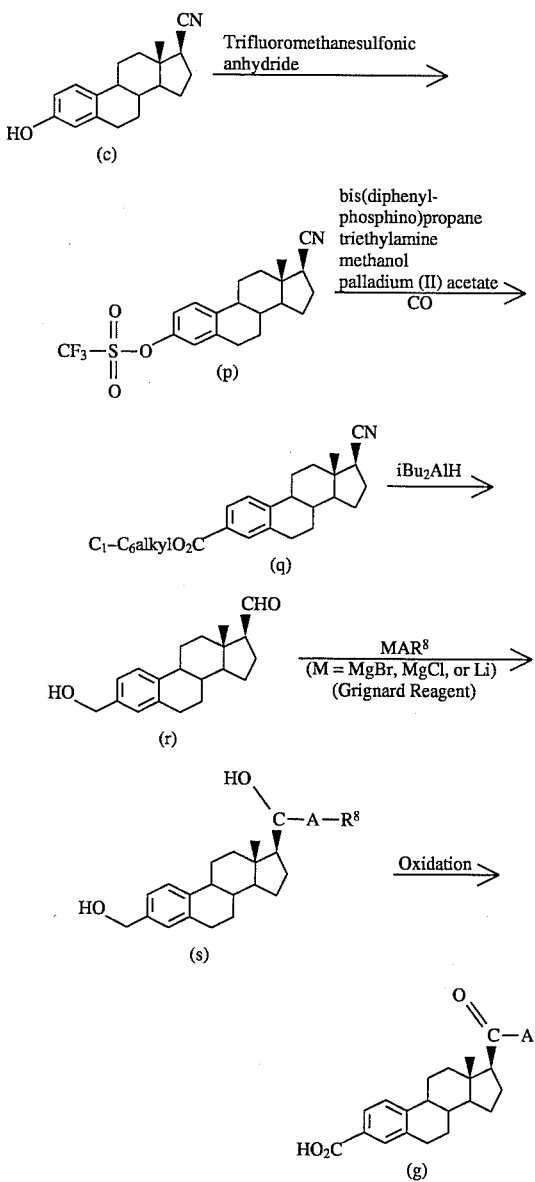

Scheme IV

Scheme IV outlines formation of Formula II compounds.

As used in Scheme IV in the alkylation process (to prepare compounds of Formula (s)), the carboxaldehyde is reacted with an Li-AR$^8$ or an XMgAR$^8$ (x=Cl, Br) Grignard reagent (as described hereinbelow), preferably benzylmagnesium chloride, 3,4-methylenedioxyphenylmagnesium bromide, 3,5-difluorophenylmagnesium bromide, 2-phenylethynylmagnesium bromide, E-2-phenylvinylmagnesium chloride, 2-furanyl lithium, 4-fluorophenethylmagnesium bromide, 2-thiophenyl lithium or 3-pyridyl lithium, preferably in tetrahydrofuran to form the desired product, preferably 17β-(benzylcarbonyl)-estra-1,3,5(10)-triene-3-carboxylic acid, 17β-(3,4-methylenedioxybenzoyl)-estra-1,3,5(10)-triene-3-carboxylic acid, 17β-(3,5-difluorobenzoyl)-estra-1,3,5(10)-triene-3-carboxylic acid, 17β-(phenylacetylenecarbonyl)-estra-1,3,5(10)-triene-3-carboxylic acid, 17β-(cinnamoyl)-estra-1,3,5(10)-triene-3-carboxylic acid, 17β-(2-furanylcarbonyl)-estra-1,3,5(10)-triene-3-carboxylic acid, 17β-(4-fluorophenethylcarbonyl)-estra-1,3,5(10)-triene-3-carboxylic acid, 17β-(2-thiophenylcarbonyl)-estra-1,3,5(10)-triene-3-carboxylic acid, or 17β-( 3-pyridylcarbonyl)-estra-1,3,5(10)-triene-3-carboxylic acid, respectively, in one or two steps.

The starting material in Scheme IV is Formula (c) compound prepared as in Scheme I.

As used in Scheme IV, a Formula (c) compound and a base, preferably 2,5-di-t-butyl-3-methyl-pyridine in an appropriate organic solvent, preferably dichloromethane, is cooled to –20° C. to 20° C., preferably 0° C., and reacted with a trihaloalkyl sulfonic anhydride, preferably trifluoromethanesulfonic anhydride to form compounds (p).

Formula (q) compounds are prepared by reacting a Formula (p) compound in a metal catalyzed coupling reaction. Preferably a Formula (p) compound dissolved in dimethylformide (DMF) and organic base preferably, triethylamine, a phosphine, preferably bis(diphenylphosphino)propane, a palladium(II) compound, preferably, palladium(II) acetate, and a $C_1$–$C_6$alkyl alcohol ($C_1$–$C_6$alkOH), followed by addition of carbon monoxide (CO). Formula (q) compounds are reacted with a reducing agent, preferably diisobutylaluminum hydride, to yield Formula (r) compounds.

Formula (s) compounds are produced by treating Formula (r) compounds with a Grignard Reagent (as described in Scheme III) in tetrahydrofuran or diethylether solvent, at a temperature of about-50° to –70° C., for 1–16 hours.

Formula (g) compounds are prepared by oxidation of Formula (s) compounds. Preferably said oxidation will utilize a Jones reagent or tetrapropylammonium perruthenate followed by sodium chlorite.

Grignard reagents of the type, XMgAR$^8$, for all of the species included within the scope of this invention, are available or can be made readily by one skilled in the art.

For example, where AR$^8$ is hydroxyphenyl, this can be derived by starting with an appropriate bromophenol, e.g. p-bromophenol, protecting the phenolic-OH with a conventional blocking group, e.g. triorganosilyl, i.e. t-butyldimethylsilyl, carrying out the Grignard reaction and then deblocking the silyl group by the use of, e.g. refluxing aqueous tetrabutylammonium fluoride.

For a AR$^8$ being hydroxyethylphenyl, the same blocking procedure can be analogously conducted starting with the appropriate hydroxyalkyl bromophenol, e.g. p-hydroxymethylbromobenzene, or p-hydroxymethylbromobenzene, or p-hydroxyethylbromobenzene.

Where a AR$^8$ is carboxyphenyl, this can be obtained by the chromic acid oxidation of the appropriate hydroxymethylbenzene, e.g. p-bromo-hydroxymethylbenzene, formed as described above.

Where a AR⁸ is —Oalkyl, the appropriate bromo-Oalkyl benzene, e.g. p-methoxybromobenzene, is utilized for the Grignard reaction.

Other halo substituted benzenes to form the appropriate Grignard reagent useful in the instant invention will be obvious to one skilled in the art from this disclosure.

Formula I compounds in which Z is in the α position are prepared from compounds which contain the corresponding β substituent by the General Method below.

General Method A

To a stirred solution of a substituted 17β steroidal 5α-reductase inhibiting compound of Formula (II) in an appropriate solvent, preferably ethylene glycol or dimethyl sulfoxide, is added a base such as a hydroxide or alkoxide base, preferably sodium hydroxide, potassium hydroxide or sodium methoxide, at a temperature over 100° C. preferably at reflux temperatures to yield the corresponding α epimer, after isolation and work up.

In determining the appropriate solvent for conducting the epimerization, dimethyl sulfoxide or other non-reactive high boiling solvents are preferred when the starting 17β5α-reductase inhibiting steroidal compound contains reactive substituents or reactive unsaturated bonds that are, for example, subject to nucleophilic attack and ethylene glycol, or other reactive high boiling solvents can be used when the reactivity of the substituents or any unsaturated bonds of the starting 17β5α-reductase inhibiting steroidal compound is not a consideration.

Also within the scope of the present invention are the ketone reduction products of Formula (I) compounds, the secondary alcohols of the formula:

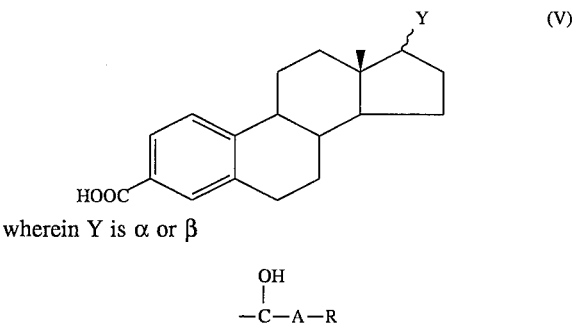

wherein Y is α or β

$$\begin{array}{c} \text{OH} \\ | \\ -\text{C}-\text{A}-\text{R} \end{array}$$

in which A is absent or present as a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR⁶ and —S(O)$_n$R⁵, where R⁶ is hydrogen or alkyl, n is 0–2 and R⁵ is hydrogen, cycloalkyl, C₆–C₁₂aryl, substituted cycloalkyl, substituted C₆–C₁₂aryl, alkyl or alkyl substituted with one or more substituents selected from the group consisting of: alkoxy, acyloxy, amino, N-acylamino, oxo, hydroxy, cycloalkyl, substituted cycloalkyl, aryloxy, —C(O)OR⁶, —S(O)$_n$R⁷, nitro, cyano, halogen, C₆–C₁₂aryl, substituted C₆–C₁₂aryl and protected —OH, where R⁶ is hydrogen or alkyl, n is 0–2 and R⁷ is hydrogen or alkyl;

b) cycloalkyl is nonaromatic, unsaturated or saturated, cyclic or polycyclic C₃–C₁₂, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR⁶, —S(O)$_n$R⁵, protected —OH and alkyl substituted with one or more substituents selected from the group consisting of: alkoxy, acyloxy, C₆–C₁₂aryl, substituted C₆–C₁₂aryl, amino, N-acylamino, oxo, hydroxy, cycloalkyl, substituted cycloalkyl, —C(O)OR⁶, —S(O)$_n$R⁷, aryloxy, nitro, cyano, halogen and protected —OH, where R⁶ is hydrogen or alkyl, n is 0–2, R⁷ is hydrogen or alkyl and R⁵ is hydrogen, cycloalkyl, C₆–C₁₂aryl, substituted cycloalkyl, substituted C₆–C₁₂aryl, alkyl or alkyl substituted with one or more substituents selected from the group consisting of: alkoxy, acyloxy, cycloalkyl, substituted cycloalkyl, aryloxy, amino, N-acylamino, oxo, hydroxy, —C(O)OR⁶, —S(O)$_n$R⁷, nitro, cyano, halogen, C₆–C₁₂aryl, substituted C₆–C₁₂aryl and protected —OH, where R⁶ is hydrogen or alkyl, n is 0–2 and R⁷ is hydrogen or alkyl; and c) aryl is cyclic or polycyclic aromatic C₃–C₁₂, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, C₆–C₁₂aryl, alkoxy, acyloxy, substituted C₆–C₁₂aryl, amino, N-acylamino, nitro, cyano, halogen, hydroxy, —C(O)OR⁶, —S(O)$_n$R⁵, protected —OH and alkyl substituted with one or more substituents selected from the group consisting of: alkoxy, acyloxy, C₆–C₁₂aryl, substituted C₆–C₁₂aryl, amino, N-acylamino, oxo, hydroxy, cycloalkyl, substituted cycloalkyl, —C(O)OR⁶, —S(O)$_n$R⁷, aryloxy, nitro, cyano, halogen and protected —OH, where R⁶ is hydrogen or alkyl, n is 0–2, R⁷ is hydrogen or alkyl and R⁵ is hydrogen, cycloalkyl, C₆–C₁₂aryl, substituted cycloalkyl, substituted C₆–C₁₂aryl, alkyl or alkyl substituted with one or more substituents selected from the group consisting of: alkoxy, acyloxy, aryloxy, amino, N-acylamino, oxo, hydroxy, —C(O)OR⁶, —S(O)$_n$R⁷, nitro, cyano, cycloalkyl, substituted cycloalkyl, halogen, C₆–C₁₂aryl, substituted C₆–C₁₂aryl and protected —OH, where R⁶ is hydrogen or alkyl, n is 0–2 and R⁷ is hydrogen or alkyl; and pharmaceutically acceptable salts, hydrates solvates and esters thereof.

Particularly preferred among the presently invented ketone reduction products described above are the secondary alcohols wherein the 17

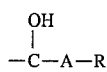

substituent is attached in the β position.

Particularly preferred among the presently invented ketone reduction products described above are 17β-(1-hydroxy-2-phenylethyl )-estra-1,3,5(10)-triene-3-carboxylic acid and 17β-(1-hydroxy-3-phenyl-2-propynyl)-estra-1,3,5(10)-triene-3-carboxylic acid.

These compounds can be made by conventional sodium borohydride reduction of the carbonyl attached to A without epimerization of the $C_{17}$ substituent or reducing the carboxyl in Ring A or the aromatic A ring. If the R substituent contains a carbonyl function, it can be selectively blocked and then regenerated after the borohydride reduction by conventional methods.

The borohydride reduction can be carried out in e.g. water or aqueous methanol, at a temperature of room temperature to 50° C. and the product then isolated and purified by conventional means. The compounds are also active as 5-alpha reductase inhibitors.

By the term "increased temperatures" as used herein and in the claims is meant above 25° C., preferably at reflux temperatures.

By the term "solvent" or "appropriate solvent" as used herein and the in the claims is meant a solvent such as methylene chloride, ethylene chloride, chloroform, ethylene glycol, carbon tetrachloride, tetrahydrofuran (THF), ethyl ether, toluene, ethyl acetate, hexane, dimethylsulfoxide (DMSO), N,N'-dimethyl-N,N'-propylene urea, N-methyl-2-pyrrolidinone, methanol, isopropylalcohol, dimethylformamide (DMF), water, pyridine, quinoline or ethanol.

Pharmaceutically acceptable salts, hydrates and solvates of Formula (I) and Formula (V) compounds are formed, where appropriate, by methods well known to those of skill in the art.

In preparing the presently invented compounds of Formula (I), novel intermediates of the following Formula (III) are synthesized;

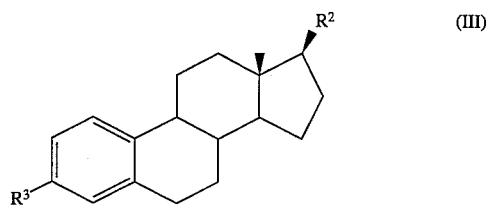

$R^2$ is 2-thiopyridylcarbonyl and $R^3$ is $C_{1-6}$alkoxycarbonyl, hydroxy, trifluoromethylsulfonyloxy or fluorosulfonyloxy.

Also, prepared in synthesizing the presently invented Formula (I) compounds were novel intermediates of the Formula (IV):

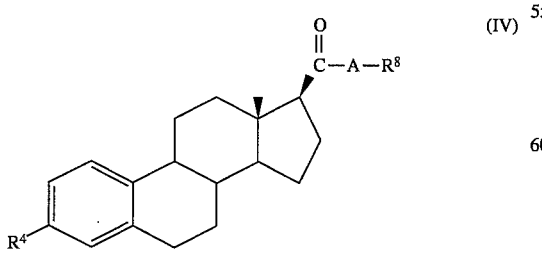

in which A is as defined in Formula (II) and $R^8$ is R as defined in Formula (II) or moieties which can be converted to those of R by known reactions such as desired in Derek Barton and U.S. Ollis, *Comprehensive Organic Chemistry: The Synthesis and Reactions of Organic Compounds*, Pub: Pergamon Press (1979), and $R^4$ is trifluoromethylsulfonyloxy, fluorosulfonyloxy or hydroxy.

Also, prepared in synthesing the presently invented Formula (I) compounds were novel intermediates of the Formula (VI)

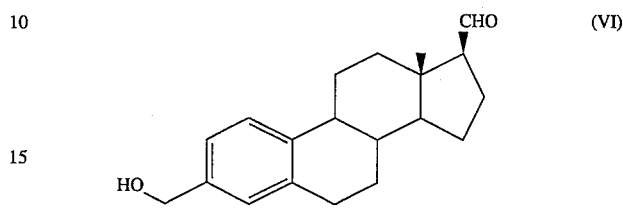

Also, prepared in synthesising the presently invented Formula (I) compounds were novel intermediates of the Formula (VII)

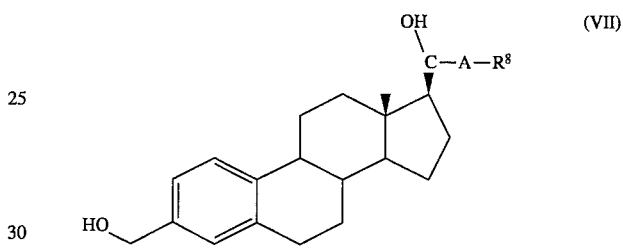

in which A and $R^8$ are as described in Formula (IV).

A preferred process for preparing a compound of Formula (II)

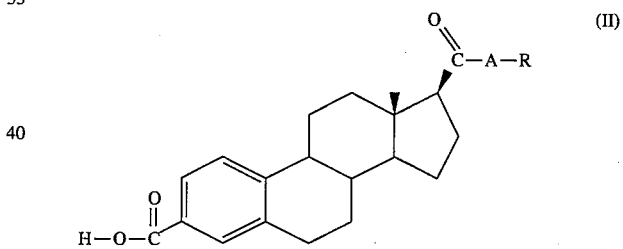

in which A is absent or present as a linear or branched, saturated or unsaturated hydrocarbon chain containing from 1–12 carbon atoms; and R is as defined in Formula (II) above and pharmaceutically acceptable salts, hydrates, solvates and esters thereof comprises reacting a compound of the formula

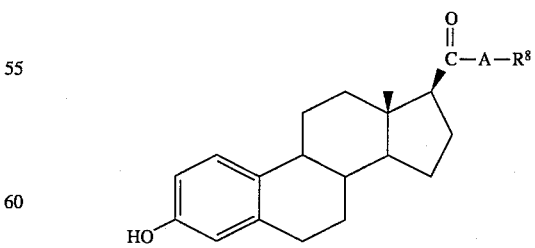

in which A is as described above and $R^8$ is as defined in Formula (IV) with fluorosulfonic anhydride and a base, preferably, 2,5-t-butyl-3-methyl-pyridine, in a solvent, preferably dichloromethane, to form a compound of the formula

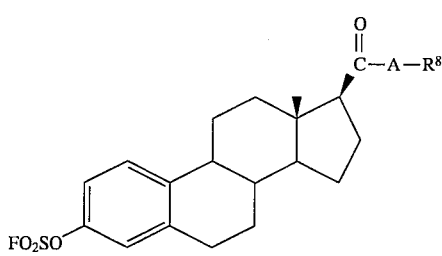

in which A and $R^8$ are as described above and subsequently reacting said compound in a metal-catalyzed coupling reaction in the presence of an appropriate coupling reagent, preferably, carbon monoxide followed by an optional, if applicable, hydrolysis reaction and optionally, if applicable, converting $R^8$ to R, and thereafter optionally forming a pharmaceutically acceptable salt, hydrate or solvate thereof.

Because the presently invented pharmaceutically active compounds inhibit steroid 5-α-reductase activity, they have therapeutic utility in treating diseases and conditions wherein decreases in DHT activity produces the desired therapeutic effect. Such diseases and conditions include acne vulgaris, seborrhea, female hirsutism, male pattern baldness, prostate diseases such as benign prostatic hypertrophy, and prostatic adenocarcinoma.

In determining potency in inhibiting the human 5α-reductase enzyme, the following procedure was employed:
Preparation of membrane particulates used as source for recombinant teroid 5α-reductase isozyme 1.

Chinese hamster ovary (CHO) cells containing expressed, recombinant human steroid 5α-reductase isoenzyme 1 (Andersson, S., Berman, D. M., Jenkins, E. P., and Russell, D. W. (1991) Nature 354 159–161) were homogenized in 20 mM potassium phosphate, pH6.5, buffer containing 0.33M sucrose, 1 mM dithiothreitol, and 50 μM NADPH (buffer A) using a Dounce glass-to-glass hand homogenizer (Kontes Glass Co., Vineland, N.J.). Membrane particulates were isolated by centrifugation (100,000×g at 4° C. for 60 minutes) and resuspended in 20 mM potassium phosphate, $pH_{6.5}$, containing 20% glycerol, 1 mM dithiothreitol, and 50 μM NADPH (buffer B). The suspended particulate solution was stored at −80° C.
Preparation of prostatic membrane particulates used as source for steroid 5α-reductase isozyme 2.

Frozen human prostates were thawed and minced into small pieces (Brinkmann Polytron (Sybron Corp., Westbury, N.Y.). The solution was sonicated for 3 to 5 minutes with a Sonifier (Branson Sonic Power Co.) followed by hand homogenization in a Dounce hand homogenizer. Prostatic particles were obtained by differential centrifugation at 600 or 1000×g for 20 minutes and 140,000× g for 60 minutes at 4° C. The pellet obtained from the 140,000×g centrifugation was washed with 5 to 10 tissue volumes of the buffer described above and centrifuged at 140,000×g. The resulting pellet was suspended in buffer B and the particulate suspension was stored at −80° C.
Preparation of membrane particulates used as source for recombinant steroid 5-α-reductase isozyme 2.

Chinese hamster ovary (CHO) cells containing expressed, recombinant human steroid 5-α-reductase isoenzyme 2 were homogenized in 20 mM potassium phosphate, pH6.5, buffer containing 0.33M sucrose, 1 mM dithiothreitol, and 50 μM NADPH (buffer A) using a Douce hand homogenizer. Membrane particulates containing the recombinant human enzyme were isolated by centrifugation (100,000×g at 4° C. for 60 minutes) and resuspended in 20 mM potassium phosphate, pH6.5 containing 20% glycerol, 1 mM dithiothreitol, and 50 μM NADPH (buffer B). The suspended particulate solution was stored at -80° C. until used.
Assay for enzymes activities and inhibitors potency.

A constant amount of [$^{14}$C]testosterone (50 to 55 mCi/mmol) in ethanol and varying amounts of potential inhibitor in ethanol were deposited in test tubes and concentrated to dryness in vacuo. To each tube was added buffer, 10 μL (recombinant isoenzyme 1 or isoenzyme 2) or 20 μL (isoenzyme 2 from human prostate tissue) of 10 mM NADPH and an aliquot of asteroid 5α-reductase preparation to a final volume of 0.5 mL. Assays for human steroid 5α-reductase isoenzyme 1 were conducted with a sample of the recombinant protein expressed in CHO cells in 50 mM phosphate buffer, pH7.5 while assays of isoenzyme 2 were conducted with a suspension of human prostatic particulates and/or recombinant protein expressed in CHO cells in 50 mM citrate buffer at pH 5.0.

After incubating the solution at 37° C. for 20 or 30 minutes the reaction was quenched by the addition of 4 mL ethyl acetate and 0.25 μmol each of testosterone, 5α-dihydrotestosterone, androstanediol, and androstanedione as carriers. The organic layer was removed to a second test tube and evaporated to dryness in a Speed Vac. The residue was dissolved in 40 μL, chloroform, spotted on an individual lane of a 20×20 cm prechannelled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan Inc., Washington, D.C.). The percent of recovered radiolabel converted to product was calculated, from which enzyme activity was determined. All incubations were conducted such that no more than 20% of the substrate (testosterone) was consumed.

The experimentally obtained data was computer fit to a linear function by plotting the reciprocal of the enzyme activity (1/velocity) against the variable inhibitor concentration; apparent inhibition constants ($K_{i,app}$) were determined by the Dixon analysis (Dixon, M. (1953).

The value for the inhibition constant (Ki) was calculated from known procedures (Levy, M. (1989), *Biochemistry*, 29:2815–2824).

All of the compounds within the scope of this invention are useful in inhibiting steroid 5-α-reductase in a mammal, including humans, in need thereof.

Compounds within the scope of this invention has been tested and has shown an activity of from 3 Ki(nM) to 110 Ki(nM) against isozyme 1 and an activity of from 1 Ki(nM) to 8 Ki(nM) against isozyme 2. Particularly preferred among the compounds of the invention and the compounds used in the invented pharmaceutical compositions and invented methods are 17β-benzoyl-estra-1,3,5(10)-triene-3-carboxylic acid,
17β-(cyclohexylcarbonyl)-estra-1,3,5(10)-triene-3-carboxylic acid,
17β-(4-fluorobenzoyl)-estra-1,3,5(10)-triene-3-carboxylic acid,
17β-(benzylcarbonyl)-estra-1,3,5(10)-triene-3-carboxylic acid,
17β-(1-naphthylcarbonyl)-estra-1,3,5(10)-triene-3-carboxylic acid,
17β-(phenethylcarbonyl)-estra-1,3,5(10)-triene-3-carboxylic acid,
17β-(cyclohexylmethylcarbonyl)-estra-1,3,5(10)-triene-3-carboxylic acid,
17β-(cyclohexylethylcarbonyl)-estra-1,3,5(10)-triene-3-carboxylic acid, 17β-(4-biphenylcarbonyl)-estra-1,3,5(10)-triene-3-carboxylic acid,
17β-(3-phenylpropylcarbonyl)-estra-1,3,5(10)-triene-3-carboxylic acid,
17β-(4-methoxybenzoyl)-estra-1,3,5(10)-triene-3-carboxylic acid,
17β-(4-phenoxybenzoyl)-estra-1,3,5(10)-triene-3-carboxylic acid, 17β-(4-trifluoromethylbenzoyl)-estra-1,3,5(10)-triene-3-carboxylic acid,
17β-(4-methylsulfonylbenzoyl)-estra-1,3,5(10)-triene-3-carboxylic acid,
17β-(4-methylthiobenzoyl)-estra-1,3,5(10)-triene-3-carboxylic acid,
17β-(3,5-difluorobenzoyl)-estra-1,3,5(10)-triene-3-carboxylic acid,
17β-(phenylacetylenecarbonyl)-estra-1,3,5(10)-triene-3-carboxylic acid,
17β-(4-methoxyphenethylcarbonyl)-estra-1,3,5(10)-triene-3-carboxylic acid,
17β-(3,4-methylenedioxybenzoyl)-estra-1,3,5(10)-triene-3-carboxylic acid,
17β-(4-hydroxyphenethylcarbonyl)-estra-1,3,5(10)-triene-3-carboxylic acid,
17β-(4-carboxyphenethylcarbonyl)-estra-1,3,5(10)-triene-3-carboxylic acid,
17β-(E-cinnamoyl)-estra-1,3,5(10)-triene-3-carboxylic acid,
17β-(2-furanylcarbonyl)-estra-1,3,5(10)-triene-3-carboxylic acid,
17β-(4-fluorophenethylcarbonyl)-estra-1,3,5(10)-triene-3-carboxylic acid,
17β-(4-methylthiophenethylcarbonyl)-estra-1,3,5(10)-triene-3-carboxylic acid,
17β-(4-methylsulfoxylphenethylcarbonyl)-estra-1,3,5(10)-triene-3-carboxylic acid,
17β-(4-methylsulfonylphenethylcarbonyl)-estra-1,3,5(10)-triene-3-carboxylic acid,
17β-(2-thiophenylcarbonyl)-estra-1,3,5(10)-triene-3-carboxylic acid,
17β-(3-pyridylcarbonyl)-estra-1,3,5(10)-triene-3-carboxylic acid,
17β-(3-pyridylmethylcarbonyl)-estra-1,3,5(10)-triene-3-carboxylic acid,
17β-(4-pyridylmethylcarbonyl)-estra-1,3,5(10)-triene-3-carboxylic acid,
17β-(2-pyridylethylcarbonyl)-estra-1,3,5(10)-triene-3-carboxylic acid,
17β-(1-hydroxy-2-phenylethyl)-estra-1,3,5(10)-triene-3-carboxylic acid and
17β-(1-hydroxy-3-phenyl-2-propynyl)-estra-1,3,5(10)-triene-3-carboxylic acid.

The pharmaceutically active compounds of the present invention are preferably incorporated into convenient dosage forms such as capsules, tablets, or injectable preparations. Solid or liquid pharmaceutical carriers are employed. Solid careers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will preferably be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.1–1000 mg/kg of active compound, preferably 1–100 mg/kg. When treating a human patient in need of steroid 5-α-reductase inhibition, the selected dose is administered preferably from 1–6 times daily, orally or parenterally. Preferred forms of parenteral administration include topically, rectally, transdermally, by injection and continuously by infusion. Oral dosage units for human administration preferably contain from 1 to 500 mg of active compound. Oral administration, which uses lower dosages is preferred. Parenteral administration, at high dosages, however, also can be used when safe and convenient for the patient.

The method of this invention of inhibiting steroid 5-α-reductase activity in mammals, including humans, comprises administering to a subject in need of such inhibition an effective steroid 5-α-reductase inhibiting amount of a pharmaceutically active compound of the present invention.

The invention also provides for the use of a compound of Formula (I) or a compound of Formula (V) in the manufacture of a medicament for use in the inhibition of steroid 5-α-reductase.

The invention also provides for a pharmaceutical composition for use in the treatment of benign prostate hypertrophy which comprises a compound of Formula I or a compound of Formula (V) and a pharmaceutically acceptable carrier.

The invention also provides for a pharmaceutical composition for use in the treatment of prostatic adenocarcinoma which comprises a compound of Formula I or a compound of Formula (V) and a pharmaceutically acceptable carrier.

The invention also provides for a process for preparing a pharmaceutical composition containing a pharmaceutically acceptable carrier or diluent and a compound of Formula I or a compound of Formula (V) which comprises bringing the compound of Formula I or the compound of Formula (V) into association with the pharmaceutically acceptable carrier or diluent.

No unacceptable toxicological effects are expected when compounds of the invention are administered in accordance with the present invention.

In addition, the pharmaceutically active compounds of the present invention can be co-administered with further active ingredients, such as other compounds known to treat the disease states of acne vulgaris, seborrhea, female hirsutism, male pattern baldness, benign prostate hypertrophy or prostatic adenocarcinoma or compounds known to have utility when used in combination with 5-α-reductase inhibitors. Particularly preferred is the co-administration of a 5-α-reductase inhibitor, as disclosed herein, and minoxidil for use in the treatment of male pattern baldness. Particularly preferred is the co-administration of a 5α-reductase inhibitor, as disclosed herein, and a α-receptor antagonist for use in the treatment of benign prostatic hypertrophy. Preferred is the co-administration of a 5-α-reductase inhibitor, as disclosed herein, and an aromatase inhibitor for use in the treatment of benign prostatic hypertrophy. Preferred is the co-administration of a 5-α-reductase inhibitor, as disclosed herein, a α-receptor antagonist and an aromatase inhibitor for use in the treatment of benign prostatic hypertrophy.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLE 1 corresponding to Scheme I 17β-Benzoyl-estra-1,3,5(10)-triene-3-carboxylic Acid (i). 17β-Cyano-estra-1,3,5(10)-triene-3-methanesulfonate.

The title compound is known and is prepared from estrone according to the procedure of Baldwin et al., *J. Chem. Soc.* (C), 1968, 2283–2289.

(ii). 17β-Cyano-estra-1,3,5(10)-trien-3-ol.

To a suspension of 17β-cyano-estra-1,3,5(10)-triene-3-methanesulfonate (10 g) in methanol (100 mL) is added dropwise a solution of NaOH (42 mL of a 20% solution in 1:1 MeOH-water). The resulting mixture is heated to 40° C. for 24 h after which time the mixture is cooled to 0° C., diluted with water (350 mL), and acidified with dilute HCl. The resulting white precipitate is isolated by vacuum filtration, washed with water, and dried under vacuum. Recrystallization from acetonitrile provides the title compound mp 249°–250° C. Dec.

(iii). 17β-Benzoyl-estra-1,3,5(10)-trien-3-ol.

17β-Cyano-estra-1,3,5(10)-trien-3-ol (1.4 g, 5 mmol) was dissolved in dry THF (20 mL) and added to a solution of phenylmagnesium bromide in THF (13 mL, 1M, 13 mmol). The resulting reaction mixture was heated at reflux for 3 h after which time it was allowed to cool to ambient temperature. To the cooled reaction mixture was then added aqueous HCl (25 mL, 6N) and the resulting reaction mixture heated again at reflux for 2 h. After cooling to ambient temperature, the THF was removed from the reaction mixture by rotary evaporation at reduced pressure and the resulting residual mixture was diluted with ethyl acetate (100 mL). The organic phase was separated and washed successively with water and brine, dried over $MgSO_4$, and evaporated to dryness. Chromatography on silica gel with 1:4 EtOAc-hexanes as eluent provided the title compound as a white solid, mp 210°–215° C.

(iv). 17β-Benzoyl-estra-1,3,5(10)-triene-3-trifluoromethanesulfonate.

A solution of 17β-benzoyl-estra-1,3,5(10)-trien-3-ol (0.18 g, 0.5 mmol) in dichloromethane (15 mL) at 0° C. was treated with 2,5-di-t-butyl-3-methyl-pyridine (0.12 g, 0.6 mmol), followed after 10 min with trifluoromethanesulfonic anhydride (0.34 g, 1.2 mmol). The resulting mixture was stirred for 2 h and then diluted with dichloromethane. The organic layer was washed with saturated aqueous $NaHCO_3$ and brine, dried over $MgSO_4$, and evaporated to dryness. Chromatography on silica gel with 1:19 EtOAc-hexanes as eluent provided the title compound as a white solid, mp 112°–114° C.

(v). Methyl 17β-Benzoyl-estra-1,3,5(10)-triene-3-carboxylate.

A mixture of 17β-benzoyl-estra-1,3,5(10)-triene-3-trifluoromethanesulfonate (0.2 g, 0.4 mmol), 1,3-bis(diphenylphosphino)propane (10 mg), palladium diacetate (5.6 mg), triethylamine (0.11 mL), methanol (0.8 mL), DMSO (1.25 mL), and 1,2-dichloroethane (0.425 mL) was heated and vigorously stirred for 5 h at 80° C. under an atmosphere of carbon monoxide. After cooling to ambient temperature, the resulting mixture was diluted with dichloromethane. The organic phase is thoroughly washed with water, dried ($MgSO_4$) and evaporated to dryness. Chromatography on silica gel with 1:9 EtOAc-hexanes as eluent provided the title compound as a white foam.

(vi). 17β-Benzoyl-estra-1,3,5(10)-triene-3-carboxylic Acid.

A mixture of methyl 17β-benzoyl-estra-1,3,5(10)-triene-3-carboxylate (60 mg, 0.15 mmol), $K_2CO_3$ (60 mg, 0.44 mmol), water (1 mL), and methanol (9 mL) was heated at reflux for 5 h. The volatiles were then removed at reduced pressure and the residue was diluted with water, acidified with dilute aqueous HCl, and extracted with EtOAc. The organic extract was washed with water and brine, dried, and evaporated to dryness. Trituration of the residue with acetone and methanol provided the title compound as a white solid, mp 240°–243° C.

EXAMPLE 2 corresponding to Scheme II 17β-Benzoyl-estra-1,3,5(10)-triene-3-carboxylic Acid (i). 17β-Cyano-estra-1,3,5(10)-triene-3-methanesulfonate.

The title compound is known and is prepared from estrone according to the procedure of Baldwin et al., *J. Chem. Soc.* (C), 1968, 2283–2289.

(ii). 17β-Cyano-estra-1,3,5(10)-trien-3-ol.

To a suspension of 17β-cyano-estra-1,3,5(10)-triene-3-methanesulfonate (10 g) in methanol (100 mL) is added dropwise a solution of NaOH (42 mL of a 20% solution in 1:1 MeOH-water). The resulting mixture is heated to 40° C. for 24 h after which time the mixture is cooled to 0° C., diluted with water (350 mL), and acidified with dilute HCl. The resulting white precipitate is isolated by vacuum filtration, washed with water, and dried under vacuum. Recrystallization from acetonitrile provides the title compound. MP. 249°–250° c. dec.

(iii). 17β-Benzoyl-estra-1,3,5(10)-trien-3-ol.

17β-Cyano-estra-1,3,5(10)-trien-3-ol (1.4 g, 5 mmol) was dissolved in dry THF (20 mL) and added to a solution of phenylmagnesium bromide in THF (13 mL, 1M, 13 mmol). The resulting reaction mixture was heated at reflux for 3 h after which time it was allowed to cool to ambient temperature. To the cooled reaction mixture was then added aqueous HCl (25 mL, 6N) and the resulting reaction mixture heated again at reflux for 2 h. After cooling to ambient temperature, the THF was removed from the reaction mixture by rotary evaporation at reduced pressure and the resulting residual mixture was diluted with ethyl acetate (100 mL). The organic phase was separated and washed successively with water and brine, dried over $MgSO_4$, and evaporated to dryness. Chromatography on silica gel with 1:4 EtOAc-hexanes as eluent provided the title compound as a white solid, mp 210°–215° C.

(iv). 17β-Benzoyl-estra-1,3,5(10)-triene-3-fluorosulfonate.

A solution of 17α-benzoyl-estra-1,3,5(10)-trien-3-ol in dichloromethane at 0° C. is treated with 2,5-di-t-butyl-3-methyl-pyridine followed after 10 min with fluorosulfonic anhydride. The resulting mixture is stirred for 2 h and then diluted with dichloromethane. The organic layer is washed with saturated aqueous $NaHCO_3$ and brine, dried over $MgSO_4$, and evaporated to dryness. Chromatography on silica gel yields the title compound.

(v). Methyl 17β-Benzoyl-estra-1,3,5(10)-triene-3-carboxylate.

A mixture of 17β-benzoyl-estra-1,3,5(10)-triene-3-fluorosulfonate 1,3-bis(diphenylphosphino)propane, palladium diacetate, triethylamine, methanol, DMSO and 1,2-dichloroethane is heated and vigorously stirred for 5 h at 80° C. under an atmosphere of carbon monoxide. After cooling to ambient temperature, the resulting mixture is diluted with dichloromethane. The organic phase is thoroughly washed with water, dried ($MgSO_4$) and evaporated to dryness. Chromatography on silica gel yields the title compound.

(vi). 17β-Benzoyl-estra-1,3,5(10)-triene-3-carboxylic Acid.

A mixture of methyl 17β-benzoyl-estra-1,3,5(10)-triene-3-carboxylate, $K_2CO_3$, water and methanol is heated at reflux for 5 h. The volatiles are then removed at reduced pressure and the residue is diluted with water, acidified with dilute aqueous HCl, and extracted with EtOAc. The organic extract is washed with water and brine, dried, and evaporated to yield the title compound.

EXAMPLE 3 corresponding to Scheme III 17β-Benzoyl-estr-1,3,5(10)-triene-3-carboxylic acid (i). 3-(trifluoromethanesulfonyloxy)-estra-1,3,5(10)-triene-17β-carboxylic acid A solution of 3-hydroxy-estra-1,3,5(10)-17β-carboxylic acid, 2,6-di-t-butyl-4-methyl pyridine and trifluoromethane sulfonic anhydride in methylene chloride is stirred at 5° C. for 20 hours. The organic solvent is evaporated and the residue is dissolved in tetrahydrofuran water (99.5:0.5) with 4-dimethylaminopyridine which upon acidification with hydrochloric acid followed by conventional workup yields title compound.

(ii). S-(2-pyridyl)-3-(trifluoromethanesulfonyloxy)-estra-1,3,5(10)-triene-17β-thiocarboxylate A solution of 3-(trifluoromethanesulfonyloxy)-estra-1,3,5(10)-triene-17β-carboxylic acid, triphenylphosphine and, 2,2'-dipyridyl disulfide in toluene is stirred under nitrogen for 20 hours. The reaction mixture is concentrated and the residue is passed directly through silica gel and appropriate fractions evaporated to yield title compound.

(iii). 17β-Benzoyl-estra-1,3,5(10)-triene-3-trifluoromethane sulfonate

To a solution of S-(2-pyridyl)-3-(trifluoromethanesulfonyloxy)-estra-1,3,5(10)-triene-17β-thiocarboxylate in tetrahydrofuran at about −50° C. is added phenylmagnesium bromide. The reaction mixture is warmed to about −10° C., and diluted with a saturated aqueous ammonium chloride solution. Conventional workup with subsequent isolation by column chromatography yields title compound.

(iv). Methyl 17β-benzoyl-estra-1,3,5(10)-triene-3-carboxylate

A solution of 17β-benzoyl-estra-1,3,5(10)-triene-3-trifluoromethane sulfonate, triphenyl phosphine, palladium II acetate, triethylamine, methanol and dimethyl formamide is stirred vigorously under a carbon monoxide atmosphere for 20 hours. Conventional workup with subsequent isolation by column chromatography yields title compound.

(v). 17β-benzoyl-estra-1,3,5(10)-triene-3-carboxylic acid

A mixture of methyl 17β-benzoyl-estra-1,3,5(10)-triene-3-carboxylate, $K_2CO_3$, water and methanol is heated at reflux for about 5 hours. Acidifications followed by conventional workup yields title compound.

EXAMPLE 4 corresponding to Scheme III 17β-Cyclohexylcarbonyl-estra-1,3,5(10)-triene-3-carboxylic Acid (i). S-(2-pyridyl)-3-hydroxy-estra-1,3,5(10)-triene-17β-thiocarboxylate.

A mixture of 3-hydroxy-estra-1,3,5(10)-triene-17β-carboxylic acid (0.11 g, 0.37 mmol), 2,2'-diipyridyl disulfide (0.163 g, 0.74 mmol), triphenylphosphine (0.19 g, 0.74 mmol) and dichloromethane (20 ml) was stirred at ambient temperature under argon for 4 hours. The resulting solution was concentrated and the residue was chromatographed (silica gel, eluting with 25 % ethyl acetate in hexane) to provide 0.13 g of the title compound as a white solid, mp 195°–196° C. (recrystallized from ethyl acetate—methanol).

(ii). 17β-Cyclohexylcarbonyl-3-hydroxy-estra-1,3,5(10)-triene.

Cyclohexylmagnesium chloride (1.9 mL; 2M in diethyl ether) was added slowly to a solution of S-(2-pyridyl)-3-hydroxy-estra-1,3,5(10)-triene-17β-thiocarboxylate (0.5 g, 1.27 mmol) in tetrahydrofuran (15 mL) at −78° C. After 1 hour, the mixture was quenched with saturated aqueous $NH_4Cl$ and extracted with ethyl acetate. The organic extract was washed with brine, dried, and concentrated. The resulting residue was chromatographed (silica gel, eluting with 15% ethyl acetate in hexane) to give a white solid (0.3 g).

(iii). Trifluoromethyl-17β-cyclohexylcarbonyl-estra-1,3,5(10)-triene-3-sulfonate.

To a cooled (0° C.) solution of 17β-cyclohexylcarbonyl-3-hydroxy-estra-1,3,5(10)-triene (0.3 g, 0.82 mmol) and 2,6-di-tert-butyl-4-methylpyridine (0.2 g, 1 mmol) in dichloromethane (25 ml) was slowly added trifluoromethane sulfonic anhydride (0.3 g, 1 mmol). The resulting solution was stirred at 0° C. for 1 hour and then at ambient temperature of 30 minutes. Additional reagents 0.2 g of base and 1.2 g of $H_2O$ were added and the mixture stirred until the reaction was completed. The reaction mixture was washed with dilute HCl, water, dilute $NaHCO_3$, brine dried and concentrated. The resulting residue was chromatographed (silica gel, 5% ethyl acetate in hexane) to provide 0.3 g of solid.

(iv). Methyl-17β-cyclohexylcarbonyl-estra-1,3,5(10)-triene-3-carboxylate.

A mixture of trifluoromethyl-17β-cyclohexylcarbonyl-estra-1,3,5 (10)-triene-3-sulfonate (0.3 g 0.6 mmol), palladium (II) acetate (8.4 mg, 0.037 mmol), 1,3-bis(diphenylphosphino)propane (dppp, 15.4 mg, 0.037 mmol ), triethylamine (0.17 mL), methanol (1.2 mL), 1,2-dichloroethane (0.64 mL), and DMSO (1.9 mL) was heated at 70°–73° C. under an atmosphere of CO overnight. The cooled reaction mixture was then diluted with dichloromethane, washed with water several times, dried and concentrated. The residue was chromatographed (silica gel, eluting with 5% ethyl acetate in hexane) to provide 0.14 g of the title compound as a foam.

(v). 17β-cyclohexylcarbonyl-estra-1,3,5(10)-triene-3-carboxylic acid.

A mixture of methyl-17β-cyclohexylcarbonyl-estra-1,3,5(10)-triene-3-carboxylate (0.14 g, 0.34 mmol), $K_2CO_3$ (0.2 g, 1.45 mmol), water (3.0 mL) and methanol (30 mL) was heated at reflux overnight. The reaction mixture was then concentrated. The residue was diluted with water, acidified with dilute HCl and extracted with ethyl acetate. The organic extract was washed with brine, dried, and concentrated. The resulting solid was washed with $CH_3CN$ and isolated by filtration from boiling ethyl acetate to give, 0. 11 g of the title compound. mp 280°–285° C. (softened at 260° C.).

EXAMPLE 5 corresponding to Scheme III

17β-(4-fluorobenzoyl)-estra-1,3,5(10)-triene-3-carboxylic Acid

The title compound was prepared according to Example 4 (i–v) by substituting 4-fluorophenylmagnesium bromide for cyclohexylmagnesium chloride in step ii mp. 251°–254° C.

EXAMPLE 6 corresponding to Scheme III 17β-(benzylcarbonyl)-estra-1,3,5(10)-triene-3-carboxylic Acid The title compound was prepared according to Example 4 (i–v) by substituting benzylmagnesium chloride for cyclohexylmagnesium chloride in step ii. mp. 181°–185° C.

EXAMPLE 7 corresponding to Scheme III 17β-(4-biphenylcarbonyl)-estra 1,3,5(10)-triene-3-carboxylic Acid (i). trifluoromethyl-17β-(4-biphenylcarbonyl)-estra-1,3,5(10)-triene-3-sulfonate The title compound was prepared according to Example 4 (i–iii) by substituting 4-biphenylmagnesium bromide for cyclohexylmagnesium chloride in step ii.

(ii). 17β-(4-biphenylcarbonyl)-estra-1,3,5(10)-triene-3-carboxylic acid

A mixture of 17β-(4-biphenylcarbonyl)-estra-1,3,5(10)-triene-3-trifluoromethane sulfonate (0.09 g, 0.158 mmol), potassium acetate (0.06 g, 0.63 mmol), palladium (II) diacetate (0.0018 g, 0.008 mmol), 1,1'-Bis(diphenylphosphino)ferrocene (dppf; 0.0175g, 0.03 mmol), in DMSO 3 ml) was purged with carbon monoxide for 2 minutes and stirred under a CO balloon at 60° C. overnight. The reaction mixture was diluted with water, acidified with 0.5N hydrochloric acid and extracted with dichloromethane. The organic layer was washed with water, dried ($MgSO_4$), and evaporated under vacuum. The residue was chromatographed (silica gel, eluting with 25% ethylacetate, 1% acetic acid in hexane) to give solid triturated with methanol-acetonitrile. yield 0.026 g (35.6%). mp 268°–270° C. (softened at 260° C.).

EXAMPLE 8 corresponding to Scheme III 17β-(1-naphthylcarbonyl)-estra-1,3,5(10)-triene-3,-carboxylic Acid (i). trifluoromethyl-17β-(1-naphthylcarbonyl)-estra-1,3,5(10)-triene-3-sulfonate The title compound was prepared according to Example 4 (i–iii) by substituting 1-naphthylmagnesium bromide for cyclohexylmagnesium chloride in step ii.

(ii). 17β-(1-naphthylcarbonyl)-estra-1,3,5(10)-triene-3-carboxylic acid

The title compound was prepared according to Example 7 (ii) by substituting trifluoromethyl-17β-(1-naphthylcarbonyl)-estra-1,3,5(10)-triene-3-sulfonate, as prepared in Example 8(i), for 17β-(4-biphenylcarbonyl)-estra-1,3,5(10)-triene-3-trifluoromethane sulfonate. mp 228° C. (softened ate 170° C.).

EXAMPLE 9 corresponding to Scheme III 17β-(Phenethylcarbonyl)-estra-1,3,5(10)-triene-3-carboxylic Acid (i). trifluoromethyl-17β-(phenethylcarbonyl)-estra-1,3,5(10)-triene-3-sulfonate The title compound was prepared according to Example 4, (i–iii) by substituting phenethylmagnesium bromide for cyclohexylmagnesium chloride in step ii.

(ii). 17β-(phenethylcarbonyl)-estra-1,3,5(10)-triene-3-carboxylic acid

The title compound was prepared according to Example 7 (ii) by substituting trifluoromethyl-17β]-(phenethylcarbonyl)-estra-1,3,5(10)-triene-3-sulfonate, as prepared in Example 9(i), for 17β-(4-biphenylcarbonyl)-estra-1,3,5(10)-triene-3-trifluoromethane sulfonate. MP 181°–183° C.

EXAMPLE 10 corresponding to Scheme III 17β-(cyclohexylmethylcarbonyl)-estra-1,3,5(10)-triene-3-carboxylic Acid (i). trifluoromethyl-17β-(cyclohexylmethylcarbonyl)-estra-1,3,5(10)-triene-3-sulfonate The title compound was prepared according to Example 4(i–iii) by substituting cyclohexylmethylmagnesium bromide for cyclohexylmagnesium chloride in step ii:

(ii). 17β-(cyclohexylmethylcarbonyl)-estra-,3,5(10)-triene-3-carboxylic acid

The title compound was prepared according to Example 7 (ii) by substituting trifluoromethyl-17β-(cyclohexylmethylcarbonyl )-estra-1,3,5(10)-triene-3-sulfonate, as prepared in Example 10 (i), for 17β-(4-biphenylcarbonyl)-estra-1,3,5(10)-triene-3-trifluoromethane sulfonate. MP 239°–241° C.

EXAMPLE 11 corresponding to Scheme III 17β-(cyclohexylethylcarbonyl)-estra-1,3,5(10)-triene-3-carboxylic Acid (i). trifluoromethyl-17β-(cyclohexylethylcarbonyl)-estra-1,3,5(10)-triene-3-sulfonate The title compound was prepared according to Example 4(i–iii) by substituting cyclohexylethylmagnesium bromide for cyclohexylmagnesium chloride in step ii.

(ii). 17β-(cyclohexylethylcarbonyl)-estra-1,3,5(10)-triene-3-carboxylic acid

The title compound was prepared according to Example 7(ii) by substituting trifluoromethyl-17β-(cyclohexylethylcarbonyl)-estra-1,3,5(10)-triene-3-sulfonate, as prepared in Example 11 (i), for 17β-(4-biphenylcarbonyl)-estra-1,3,5(10)-triene-3-trifluoromethane sulfonate. MP 250°–253° C. (softened ate 247° C.)

EXAMPLE 12 corresponding to Scheme III

17β-Benzoyl-estr-1,3,5(10)-triene-3-carboxylic acid
(i). 3-(fluorosulfonyloxy)-estra-1,3,5(10)-triene-17β-carboxylic acid A solution of 3-hydroxy-estra-1,3,5(10)-17β-carboxylic acid, 2,6-di-t-butyl-4-methyl pyridine and fluorosulfonic anhydride in methylene chloride is stirred at 5° C. for 20 hours. The reaction mixture is washed with aqueous hydrochloric acid and water. The organic phase is concentrated and the resulting residue is purified by column chromatography to yield the title compound.

(ii). S-(2-pyridyl)-3-(fluorosulfonyloxy)-estra-1,3,5(10)-triene-17β-thiocarboxylate A solution of 3-(fluorosulfonyloxy)estra-1,3,5(10)-triene-17β-carboxylic acid, triphenylphosphine and, 2,2'-dipyridyl disulfide in toluene is stirred under nitrogen for 20 hours. The reaction mixture is concentrated and the residue is passed directly through silica gel and appropriate fractions evaporated to yield title compound.

(iii). 17β-Benzoyl-estra-1,3,5(10)-triene-3-fluorosulfonate

To a solution of S-(2-pyridyl)-3-(fluorosulfonyloxy)-estra-1,3,5(10)-triene-17β-thiocarboxylate in tetrahydrofuran at about -50° C. is added phenylmagnesium bromide. The reaction mixture is warmed to about −10° C. and diluted with a saturated aqueous ammonium chloride solution. Conventional workup with subsequent isolation by column chromatography yields title compound.

(iv). Methyl 17β-benzoyl-estra-1,3,5(10)-triene-3-carboxylate

A solution of 17β-benzoyl-estra-1,3,5(10)-triene-3-fluorosulfonate, triphenyl phosphine, palladium II acetate, triethylamine, methanol and dimethyl formamide is stirred vigorously under a carbon monoxide atmosphere for 20 hours. Conventional workup with subsequent isolation by column chromatography yields title compound.

(v). 17β-benzoyl-estra-1,3,5(10)-triene-3-carboxylic acid

A mixture of methyl 17β-benzoyl-estra-1,3,5(10)-triene-3-carboxylate, $K_2CO_3$, water and methanol is heated at reflux for about 5 hours. Acidification followed by conventional workup yields title compound.

EXAMPLE 13 corresponding to Scheme III 17β-(3-phenylpropylcarbonyl)-estra=1,3,5(10)triene-3-carboxylic acid (i) trifluoromethyl-17β-(3-phenylpropylcarbonyl)-estra-1,3,5(10)triene-3-sulfonate.

The title compound was prepared according to Example 4 (i)–(iii) by substituting 3-phenylpropylmagnesium bromide for cyclohexylmagnesium chloride in step ii.

(ii) 17β-(3-phenylpropylcarbonyl)-estra-1,3,5(10)triene-3-carboxylic acid.

The title compound was prepared according to Example 7 (ii) by substituting trifluoromethyl-17β-(3-phenylpropylcarbonyl )-estra-1,3,5(10)triene-3-sulfonate for 17β-(4-biphenylcarbonyl )-estra-1,3,5(10)triene-3-trifluoromethane sulfonate. mp 183°–185° C.

EXAMPLE 14 corresponding to Scheme III 17β-(4-methoxybenzoyl)-estra-1,3,5(10)triene, 3-carboxylic acid (i) trifluoromethyl-17β-(4-methoxybenzoyl)-estra-1,3,5(10)triene-3-sulfonate.

The title compound was prepared according to Example 4 (i)–(iii) by substituting 4-methoxyphenylmagnesium bromide for cyclohexylmagnesium chloride in step ii.

(ii) 17β-(4-methoxybenzoyl)-estra-1,3,5(10)triene-3-carboxylic acid.

The title compound was prepared according to Example 7 (ii) by substituting trifluoromethyl-17β-(4-methoxybenzoyl)-estra-1,3,5(10)triene-3-sulfonate for 17β-(4-biphenylcarbonyl)-estra-1,3,5(10)triene-3-trifluoromethane sulfonate. mp 259°–263° C.

EXAMPLE 15 corresponding to Scheme III 17β-(4-phenoxybenzoyl)-estra-1,3,5(10)triene-3-carboxylic acid (i) trifluoromethyl-17β-(4-phenoxybenzoyl)-estra-1,3,5(10)triene-3-sulfonate.

The title compound was prepared according to Example 4 (i)–(iii) by substituting 4-phenoxyphenylmagnesium bromide for cyclohexylmagnesium chloride in step ii.

(ii) 17β-(4-phenoxybenzoyl)-estra-1,3,5(10)triene-3-carboxylic acid.

The title compound was prepared according to Example 7 (ii) by substituting trifluoromethyl-17β-(4-phenoxybenzoyl)-estra-1,3,5(10)triene-3-sulfonate for 17β-(4-biphenylcarbonyl)-estra-1,3,5(10)triene-3-trifluoromethane sulfonate. mp 224°–225° C.

EXAMPLE 16 corresponding to Scheme III 17β-(4-trifluoromethylbenzoyl)-estra-1,3,5(10)triene-3-carboxylic acid, (i) trifluoromethyl-17β-(4-trifluoromethylbenzoyl)-estra-1,3,5(10)triene-3-sulfonate.

The title compound was prepared according to Example 4 (i)–(iii) by substituting 4-trifluoromethylphenylmagnesium bromide for cyclohexylmagnesium chloride in step ii.

(ii) 17β-(4-trifluoromethylbenzoyl)-estra-1,3,5(10)triene-3-carboxylic acid.

The title compound was prepared according to Example 7 (ii) by substituting trifluoromethyl-17β-(4-trifluoromethylbenzoyl)-estra-1,3,5(10)triene-3-sulfonate for 17β-(4-biphenylcarbonyl)-estra-1,3,5(10)triene-3-trifluoromethane sulfonate. mp 300°–303° C.

EXAMPLE 17 corresponding to Scheme III 17β-(4-methylthiobenzoyl)-estra-1,3,5(10)triene-3-carboxylic acid (i) trifluoromethyl-17β-(4-methylthiobenzoyl)-estra-1,3,5(10)triene-3-sulfonate.

The title compound was prepared according to Example 4 (i)–(iii) by substituting 4-methylthiophenylmagnesium bromide for cyclohexylmagnesium chloride in step ii.

(ii) 17β-(4-methylthiobenzoyl)-estra-1,3,5(10)triene-3-carboxylic acid.

The title compound was prepared according to Example 7 (ii) by substituting trifluoromethyl-17β-(4-methylthiobenzoyl)-estra-1,3,5(10)triene-3-sulfonate for 17β-(4-biphenylcarbonyl)-estra-1,3,5(10)triene-3-trifluoromethane sulfonate. mp 255°–257° C.

EXAMPLE 18 corresponding to Scheme III 17β-(4-methoxyphenethylcarbonyl)-estra-1,3,5(10)triene-3-carboxylic acid (i) trifluoromethyl-17β-(4-methoxyphenethylcarbonyl)-estra-1,3,5(10)triene-3-sulfonate.

The title compound was prepared according to Example 4 (i)–(iii) by substituting 4-methoxyphenethylmagnesium bromide for cyclohexylmagnesium chloride in step ii.

(ii) 17β-(4-methoxyphenethylcarbonyl)-estra-1,3,5(10)triene-3-carboxylic acid.

The title compound was prepared according to Example 7 (ii) by substituting trifluoromethyl-17β-(4-methoxyphenethylcarbonyl)-estra-1,3,5(10)triene-3-sulfonate for 17β-(4-biphenylcarbonyl)-estra-1,3,5(10)triene-3-trifluoromethane sulfonate. mp 178°–179° C.

EXAMPLE 19 corresponds to Scheme IV 17β-Benzylcarbonyl-estra-1,3,5(10)-triene-3-carboxylic acid.

(i) 17β-Cyano-estra-1,3,5(10)-triene-3-trifluoromethanesulfonate.

17β-Cyano-estra-1,3,5(10)triene-3-ol (4.2 g) and 2,6-di-t-butyl-4-methylpyride (3.6 g) was dissolved in 50 ml of methylene chloride. The mixture was stirred at room temperature for 30 min. Triflic anhydride (4.2 ml) was added and the mixture was stirred another 40 mins, diluted with 50 ml $CH_2Cl_2$, filtered, concentrated, and chromatographed on silica gel. Elution with 20% ethyl acetate in hexane gave 5.3 g (87%) of the title compound, mp 115°–117° C.

(ii) Methyl 17β-cyano-estra-1,3,5(10)triene-3-carboxylate.

To a solution of 17β-cyano-estra-1,3,5(10)triene-3-ol (10 g) in 77 ml of DMSO and 50 ml of MeOH was added 7 ml of triethylamine, 0.35 g of palladium acetate, 0.64 g of bis(diphenylphosphino)propane and 1,2-dichloroethane (26 ml). Carbon monoxide was bubbled through the solution and the reaction mixture was then stirred at 75° C. overnight under 1 atm of CO (balloon). The mixture was diluted with EtOAc and washed with water (3×), dried, and concentrated. The residue was chromatographed (silica gel, eluting with 10% EtOAc in hexane) to provide 4.5 g of the title compound, mp 161°–163° C.

(iii) 3-Hydroxymethyl-estra-1,3,5(10)-17β-carboxaldehyde.

Methyl-17β-cyano-estra-1,3,5(10)-3-carboxylate (0.8 g) was dissolved in 30 ml of toluene and treated with DIBAL (6 ml, 1M) The mixture was stirred at room temp under argon for 2.5 hours. The mixture was then poured into 50 ml of 5% $H_2SO_4$ and the mixture was stirred for 1 hour, filtered, dried, and concentrated. The residue was chromatographed (silica gel eluting with 20% EtOAc in hexane) to provide 424 mg of the title compound, mp 146°–150° C.

(iv) 3-Hydroxymethyl-20-hydroxy-21-phenyl-19-norpregna-1,3,5(10)-triene.

A solution of 3-hydroxymethyl-estra-1,3,5(10)-17β-carboxaldehyde (149 mg in 3 ml of THF) was added slowly to a solution of benzylmagnesium chloride (2.5 ml, 2.0M). The mixture was stirred at room temp for 2 hours. The mixture was quenched with saturated aqueous $NH_4Cl$ and extracted with $CH_2Cl_2$. The organic extract was washed with brine, dried, and concentrated. The resulting residue was chromatographed (silica gel, eluting with 30% EtOAc in hexane ) to give 159 mg of the title compound.

(v) 17β-Benzylcarbonyl-estra-1,3,5(10)triene-3-carboxylic acid.

3-Hydroxymethyl-20-hydroxy-21-phenyl-19-norpregna-1,3,5(10)-triene (159 mg) was dissolved in acetone (5 ml) and treated with Jones reagent. The mixture was stirred for 1 hour and then quenched with 2-propanol, extracted with $CH_2Cl_2$ and purified by chromatography (silica gel, eluting with 30% EtOAc in hexane with 0.5% HOAc added) to give 137 mg of the title compound, mp 181°–185° C.

EXAMPLE 20 corresponding to Scheme IV 17β-(3,5-difluorobenzoyl)-estra-1,3,5(10)triene-3-carboxylic acid The title compound was prepared according to Example 19 (i)–(v) by substituting 3,5-difluorophenylmagnesium bromide for benzylmagnesium chloride in step iv. mp 258°–261° C.

EXAMPLE 21 corresponding to Scheme IV 17β-(phenylacetylenecarbonyl)-estra-1,3,5(10)triene-3-carboxylic acid The title compound was prepared according to Example 19 (i)–(v) by substituting 2-phenylethynylmagnesium bromide for benzylmagnesium chloride in step iv. mp 174°–178° C.

EXAMPLE 22 corresponding to Scheme IV 17β-(cinnamoyl)-estra-1,3,5(10)triene-3-carboxylic acid The title compound was prepared according to Example 19 (i)–(v) by substituting E-2-phenylvinylmagnesium chloride for benzylmagnesium chloride in step iv. mp 177°–181° C.

EXAMPLE 23 corresponding to Scheme IV 17β-(2-furanylcarbonyl)-estra-1,3,5(10)triene-3-carboxylic acid (i) 3-hydroxymethyl-17β-(1-hydroxy-1-(2-furanyl)methyl)-1,3,5(10)-triene The title compound was prepared according to Example 19 (i)–(v) by substituting 2-furanyl lithium for benzylmagnesium chloride in step iv.

(ii) 17β-(2-furanylcarbonyl)-estra-1,3,5(10)triene-3-carboxylic acid

The title compound was prepared according to Example 27 (ii)–(iii) by substituting 3-hydroxymethyl-17β-(1-hydroxy-1-(2-furanyl)methyl)-1,3,5(10)-triene for 3-hydroxymethyl-20-hydroxy-21-(3,4-methylenedioxyphenyl)-19-norpregna-1,3,5(10)-triene in step ii. mp 180°–182° C.

EXAMPLE 24 corresponding to Scheme IV 17β-(4-fluorophenethylcarbonyl)-estra-1,3,5(10)triene-3-carboxylic acid The title compound was prepared according to Example 19 (i)–(iv) by substituting 4-fluorophenethylmagnesium bromide for benzylmagnesium chloride in step iv. mp 224°–227° C.

EXAMPLE 25 corresponding to Scheme IV 17β-(2-thiophenylcarbonyl)-estra-1,3,5(10)triene-3-carboxylic acid (i) 3-hydroxymethyl-17β-(1-hydroxy-1-(2-thiophenyl)methyl)-1,3,5(10)-triene The title compound was prepared according to Example 19 (i)–(v) by substituting 2-thiophenyl lithium for benzylmagnesium chloride in step iv.

(ii) 17β-(2-thiophenylcarbonyl)-estra-1,3,5(10)triene-3-carboxylic acid

The title compound was prepared according to Example 27 (ii)–(iii) by substituting 3-hydroxymethyl-17β-(1-hydroxy-1-(2-thiophenyl)methyl)-1,3,5(10)-triene for 3-hydroxymethyl-20-hydroxy-21-(3,4-methylenedioxyphenyl)-19-norpregna-1,3,5(10)-triene in step ii. mp 177°–179° C.

EXAMPLE 26 corresponding to Scheme IV 17β-(3-pyridylcarbonyl)-estra-1,3,5(10)triene-3-carboxylic acid (i) 3-hydroxymethyl-17β-(1-hydroxy-1-(3-pyridyl)methyl)-1,3,5(10)-triene.

The title compound was prepared according to Example 19 (i)–(v) by substituting 3-pyridyl lithium for benzylmagnesium chloride in step iv.

(ii) 17β-(3-pyridylcarbonyl)-estra-1,3,5(10)triene-3-carboxylic acid.

The title compound was prepared according to Example 27 (ii)–(iii) by substituting 3-hydroxymethyl-17β-(1-hydroxy-1-(3-pyridyl)methyl)-1,3,5(10)-triene for 3-hydroxymethyl-20-hydroxy-21-(3,4-methylenedioxyphenyl)-19-norpregna-1,3,5(10)-triene in step ii. mp 189°–192° C.

EXAMPLE 27 corresponding to Scheme IV 17β-(3,4-Methylenedioxybenzoyl)-estra-1,3,5(10)-triene-3-carboxylic acid.

(i) 3-Hydroxymethyl-20-hydroxy-21-(3,4-methylenedioxyphenyl)-19-norpregna-1,3,5(10)-triene.

The title compound was prepared by the method of Example 19 (iv) by replacing benzylmagnesium chloride with 3,4-methylenedioxyphenylmagnesium bromide.

(ii) 17β-(3,4-Methylenedioxybenzoyl)-estra-1,3,5(10)-triene-3-carboxaldehyde.

TPAP (Tetrapropylammonium perruthenate, 9 mg) was added in one portion to a mixture of 3-hydromethyl-20-hydroxy-21-(3,4-methylenedioxyphenyl)-19-norpregna-1,3,5(10)-triene (100 mg), 4-methylmorpholine N-oxide (88 mg), molecular sieves (4A, activated powder, 250 mg) and $CH_2Cl_2$ (25 ml). After stirring for 2 hours under argon, the reaction mixture was concentrated and chromatographed (silica gel, eluting with 15% EtOAC in hexane) to provide 50 mg of the title compound as a white solid.

(iii) 17β-(3,4-Methylenedioxybenzoyl)-estra-1,3,5(10)-triene-3-carboxylic acid.

To a stirred mixture of 17β-(3,4-methylenedioxybenzoyl)-estra-1,3,5(10)-triene-3-carboxaldehyde (0.041 g, 0,1 mmoles), tert-butyl alcohol (1.05 mL), 2-methyl-2-butene (4 mL of 2M solution in THF, 8 mmoles) at 0° C. was added a solution of $NaClO_2$ (9 mg, 0.1 mmoles) and $NaH_2PO_4 \cdot H_2O$ (0.137 g, 0.1 mmoles) in $H_2O$ (0.4 ml) and stirred for 2 hours at ambient temperature. Acetic acid (glacial, 0.8 ml) and saturated NaCl solution (1.3 mL) were added to the reaction mixture which was extracted with EtOAc. The organic layer was washed with $H_2O$, brine, dried ($MgSO_4$), concentrated and azetroped with toluene. The resulting solid was triturated with $CH_3CN$- acetone and filtered to give 0.02 g (47%) of the title compound as a white solid, mp 235°–237° C.

EXAMPLE 28 corresponding to Scheme III 17β-[3-(4-hydroxyphenyl)propionyl]-estra-1,3,5(10)-triene-3-carboxylic acid (i) Methyl 17β-(4-methoxyphenethylcarbonyl)-estra-1,3,5(10)-triene-3-carboxylate.

The title compound is prepared according to Example 4(i–iv) by substituting 4-methoxyphenethylmagnesium bromide for cyclohexylmagnesium chloride in step ii.

(ii) Methyl-17β-[3-(4-hydroxyphenethyl)carbonyl]-estra-1,3,5(10)-triene-3-carboxylate.

To a 0° C. solution of methyl 17β-(4-methoxyphenethylcarbonyl)-estra-1,3,5(10)-triene-3-carboxylate (0.8 g., 1.74 mmoles) in $CH_2Cl_2$ (120 ml) was added a $CH_2Cl_2$ solution of boron tribromide (7.0 ml, 1M, 7 mmoles). The resulting solution was stirred at 0° C. for 1 hour and at ambient temperature for 1.5 hours. After cooling to 0° C., methanol (25 ml) was added carefully, and stirred for 1 hour at ambient temperature. The residue obtained on evaporation of the volatiles was redissolved in EtOAc and washed with $H_2O$, brine, dried and concentrated. The resulting residue was chromatographed (silica Gel) eluting with 25% EtOAc in hexane to give yellow foam (0.35 g, 45%).

(iii) 17β-[3-(4-hydroxyphenyl)propionyl]-estra-1,3,5(10)-triene-3-carboxylic acid.

A mixture of the methyl-17β-[3-(4-hydroxyphenethyl)carbonyl]-estra-1,3,5(10)-triene-3-carboxylate (80 mg, 0.18 mmoles), $K_2CO_3$, (0.1 g, 0.7 mmoles), MeOH (9 ml) and $H_2O$ (1 ml) was refluxed under argon for 5 hours. Methanol was evaporated and the residue was acidified with dilute HCl. Extracted with EtOAc. The organic layer was washed with $H_2O$, brine and dried and concentrated. The residue was chromatographed (silica gel) eluting with 25% EtOAc in hexane containing 1% HOAc to provide pure product (foam). Triturated with $CH_3CN$ to give white solid 36.8 mg (47%), mp 197° C.

EXAMPLE 29 corresponding to Scheme III. 17β-[3-(4-carboxyphenyl)propionyl]-estra-1,3,5(10)-triene-3-carboxylic acid (i) Methyl-17β-[3-(4-trifluoromethylsulfonyloxyphenyl)propionyl]-estra-1,3,5(10)-triene-3-carboxylate.

Trifluoromethanesulfonic anhydride (0.25 g, 0.9 mmoles) was added to a mixture of methyl-17β-[3-(4-hydroxyphenyl)propionyl]-estra-1,3,5(10)-triene-3-carboxylate (0.27 g, 0.6 mmoles) (prepared according to Example 28(ii)), 2,6-di-tert-butyl-4-methylpyridine (0.15 g. 0.73 mmoles) and $CH_2Cl_2$ (10 ml). After stirring for 4 hours at ambient temperature the reaction mixture was washed successively with ice-water, dil HCl, water, 5% $NaHCO_3$, brine, dried and concentrated. The resulting residue was chromatographed (silica gel) eluting with hexane then 10% EtOAc in hexane to give the title compound (0.23 g).

(ii) Methyl-17β-[3-(4-carboxyphenyl)propionyl]-estra-1,3,5(10)-triene-3-carboxylate.

A mixture of methyl-17β-[3-(4-trifluoromethylsulfonyloxyphenyl)propionyl]-estra-1,3,5(10)-triene-3-carboxylate (0.22 g, 0.38 mmoles), potassium acetate (0.15 g, 1.58 mmoles), palladium (II) acetate (4.5 mg, 0.02 mmoles), dppf (1,1'-Bis(diphenylphosphino)ferrocene, 45 mg, 0.08 mmoles) and DMSO (15 ml) was heated at 60° C. under atmosphere of CO overnight. Since reaction was incomplete by tlc (20% EtOAc in hexane containing 1% HOAC), more reagents (same amount as above) were added and the reaction was continued for 4 hours. Reaction mixture was diluted with water, acidified with dilute HCl, and extracted with $CH_2Cl_2$ the organic layer was washed with water several times, brine, dried and concentrated. The residue was chromatographed (silica gel) eluting with 20% EtOAc in hexane containing 1% HOAC). Product was triturated with $CH_3CN$ to provide 0.053 g (29%).

(iii) 17β-[3-(4-carboxyphenyl)propionyl]-estra-1,3,5(10)-triene-3-carboxylic acid.

A mixture of methyl-17β-[3-(4-carboxyphenyl)propionyl]-estra-1,3,5(10)-triene-3-carboxylate (0.053 g, 0.11 mmoles), $K_2CO_3$ (50 mg, 0.36 mmoles), MeOH (9 ml) and $H_2O$ (1 ml) was refluxed under argon. Methanol was evaporated and the residue was acidified with dilute HCl. Extracted with EtOAc. The organic layer was washed with $H_2O$, brine, dried and concentrated. The residue was chromatographed (silica gel) eluting with 1% MeOH in $CH_2Cl_2$ containing 1% HOAC to give the title compound as a white solid (40 mg, 80%), mp 285°–290° C.

EXAMPLE 30 corresponding to Scheme III 17β-(p-Methylsulfonylbenzoyl)-estra-1,3,5(10)-triene-3-carboxylic acid.

A suspension of 17β-(p-methylthiobenzoyl)-estra-1,3,5(10)-triene-3-carboxylic acid (0.02 g, 0.046 mmoles) (prepared according to Example 17 (i)–(ii)) in 2 mL of glacial acetic acid was treated with hydrogen peroxide (2mL of 30% solution in water). After stirring for 2 hours at 60° C., the reaction mixture was concentrated, azlotroped with toluene. Resulting solid was stirred with MeOH and filtered to give 8.5 mg of white solid (40%), mp 283°–286° C.

EXAMPLE 31 corresponding to Scheme IV 17β-[1(R)-Hydroxy-2-phenylethyl]-estra-1,3,5(10)triene-3-carboxylic acid and 17β-[1(S)-Hydroxy-2-phenylethyl]-estra-1,3,5(10)triene-3-carboxylic acid.

(i) A solution of 17β-benzylcarboxyl-estra-1,3,5(10)triene-3-carboxylic acid (50mg in 10 ml of MeOH and 1 ml of H$_2$O) prepared according to Example 19 (i)–(v) was treated with 2 eq of LiBH$_4$. The mixture was warmed to 40° C. and stirred overnight. EtOAc was added and the mixture was filtered, dried and concentrated. Chromatography (silica gel, eluting 30% EtOAc in hexane with 0.5% HOAc) provided the title compounds of undetermined C-20 stereochemistry; mp 208°–213° C. (major, first eluting), and 207°–211° C. (minor, second eluting). (ii) Pure (R) and (S) forms are obtained by separation techniques readily available and known to those of skill in the art.

EXAMPLE 32 corresponding to Scheme IV 17β-[1-(R,S)-Hydroxy-3-phenylpropynyl]-estra-1,3,5(10)triene-3=carboxylic acid (i) The title compound was prepared according to Example 31 by substituting 17β-(phenylacetylenecarbonyl)-estra-1,3,5(10)triene-3-carboxylic acid for 17β-benzylcarboxyl-estra-1,3,5(10)triene-3-carboxylic acid. mp 180°–183° C.
(ii) Pure (R) and (S) forms are obtained by separation techniques readily available and known to those of skill in the art.
Example 33 corresponding to Scheme III 17 β-(4-methylthiophenethylcarbonyl)-estra-1,3,5(10)-triene-3-carboxylic acid.

(i) trifluoromethyl-17β-(4-methylthiophenethylcarbonyl)-estra-1,3,5(10)-triene-3-sulfonate.
The title compound is prepared according to Example 4 (i)–(iii) by substituting 4-methylthiophenethylmagnesium bromide for cyclohexylmagnesium chloride in step ii.
(ii) 17β-(4-methylthiophenethylcarbonyl)-estra-1,3,5(10)-triene-3-carboxylic acid.
The title compound is prepared according to Example 7 (ii) by substituting trifluoromethyl-17β-(4-methylthiophenethylcarbonyl)-estra-1,3,5(10)-triene-3-sulfonate for 17β-(4-biphenylcarbonyl)-estra-1,3,5(10)-triene-3-trifluoromethanesulfonate.

EXAMPLE 34 corresponding to Scheme III 17β-(p-methylsulfonylphenethylcarbonyl)-estra-1,3,5(10)-triene-3-carboxylic acid, The title compound is prepared according to Example 30 by substituting 17β-(4-methylthiophenethylcarbonyl)-estra-1,3,5(10)-triene-3-carboxylic acid (prepared as in Example 33 (i)–(ii)) for 17β-(p-methylthiobenzoyl)-estra-1,3,5(10)-triene-3-carboxylic acid.

EXAMPLE 35 corresponding to Scheme III 17β-(4-methylsulfoxylphenethylcarbonyl)-estra-1,3,5(10)-triene-3-carboxylic acid.

(i) 17β-(4-methylthiophenethylcarbonyl)-estra-1,3,5(10)-triene-3-carboxylic acid.
The title compound is prepared according to Example 33 (i)–(ii).
(ii) 17β-(4-methylsulfoxylphenethylcarbonyl)-estra-1,3,5(10)-triene-3-carboxylic acid. 17β-(4-methylthiophenethylcarbonyl)-estra-1,3,5(10)-triene-3-carboxylic acid in acetic acid and water is treated with K$_2$S$_2$O$_8$. After stirring at increased temperatures the reaction mixture is concentrated then azeotroped with toluene. The resulting solid is stirred with MeOH and filtered to give title compound.

EXAMPLE 36 corresponding to Scheme IV 17β-(3-pyridylmethylcarbonyl)-estra-1,3,5(10)-triene-3-carboxylic acid.

The title compound is prepared according to Example 26 (i)–(ii) by substituting 3-pyridylmethylmagnesium bromide for 3-pyridyllithium in step i.

EXAMPLE 37 corresponding to Scheme IV 17β-(4-pyridylmethylcarbonyl)-estra-1,3,5(10)-triene-3-carboxylic acid.

The title compound is prepared according to Example 26 (i)–(ii) by substituting 4-pyridylmethylmagnesium bromide for 3-pyridyllithium in step i.

EXAMPLE 38 corresponding to Scheme IV 17β-(2-pyridylethylcarbonyl)-estra-1,3,5(10)-triene-3-carboxylic acid.

The title compound is prepared according to Example 26 (i)–(ii) by substituting 2-pyridylethyl magnesium bromide for 3-pyridyllithium in step i.

EXAMPLE 39 corresponding to General Method A, 17α-Benzoyl-estra-1,3,5(10)-triene-3-carboxylic Acid Into a 250 ml 3-neck round bottom flask is placed 17β-Benzoyl-estra-1,3,5(10)-triene-3-carboxylic acid and an excess of sodium hydroxide. To the flask is added dimethyl sulfoxide as a solvent. The mixture is heated to reflux for 3 hours. Standard workup followed by isolation by preparative HPLC yields title compound.

EXAMPLE 40

An oral dosage form for administering Formula I compounds or Formula (V) compounds is produced by screening, mixing, and filling into hard gelatin capsules the ingredients in the proportions shown in Table 1, below.

TABLE I

| Ingredients | Amounts |
| --- | --- |
| 17β-Benzoyl-estra-1,3,5(10)-triene-3-carboxylic acid | 50 mg |
| magnesium stearate | 5 mg |
| lactose | 75 mg |

EXAMPLE 41

The sucrose, calcium sulfate dihydrate and Formula (I) compound or Formula (V) compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
| --- | --- |
| 17β-benzylcarbonyl-estra-1,3,5(10)-triene-3-carboxylic acid | 100 mg |
| calcium sulfate dihydrate | 150 mg |
| sucrose | 20 mg |
| starch | 10 mg |
| talc | 5 mg |
| stearic acid | 3 mg |

EXAMPLE 42

17β-Benzoyl-estra-1,3,5(10)-triene-3-carboxylic acid, 75 mg, is dispersed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the formula:

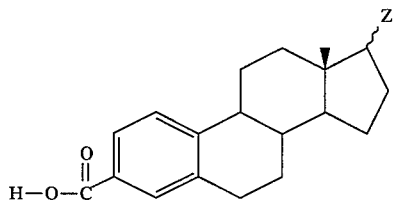

wherein Z is α or β

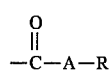

in which A is absent or present as a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, $-C(O)OR^6$ and $-S(O)_nR^5$, where $R^6$ is hydrogen or alkyl, n is 0–2 and $R^5$ is hydrogen, cycloalkyl, $C_6-C_{12}$aryl, substituted cycloalkyl, substituted $C_6-C_{12}$aryl, alkyl or alkyl substituted with one or more substituents selected from the group consisting of:

alkoxy, acyloxy, amino, N-acylamino, oxo, hydroxy, cycloalkyl, substituted cycloalkyl, aryloxy, $-C(O)OR^6$, $-S(O)_nR^7$, nitro, cyano, halogen, $C_6-C_{12}$aryl, substituted $C_6-C_{12}$aryl and protected $-OH$, where $R^6$ is hydrogen or alkyl, n is 0–2 and $R^7$ is hydrogen or alkyl;

b) cycloalkyl is nonaromatic, unsaturated or saturated, cyclic or polycyclic $C_3-C_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, $-C(O)OR^6$, $-S(O)_nR^5$, protected $-OH$ and alkyl substituted with one or more substituents selected from the group consisting of: alkoxy, acyloxy, $C_6-C_{12}$aryl, substituted $C_6-C_{12}$aryl, amino, N-acylamino, oxo, hydroxy, cycloalkyl, substituted cycloalkyl, $-C(O)OR^6$, $-S(O)_nR^7$, aryloxy, nitro, cyano, halogen and protected $-OH$, where $R^6$ is hydrogen or alkyl, n is 0–2, $R^7$ is hydrogen or alkyl and $R^5$ is hydrogen, cycloalkyl, $C_6-C_{12}$aryl, substituted cycloalkyl, substituted $C_6-C_{12}$aryl, alkyl or alkyl substituted with one or more substituents selected from the group consisting of:

alkoxy, acyloxy, cycloalkyl, substituted cycloalkyl, aryloxy, amino, N-acylamino, oxo, hydroxy, $-C(O)OR^6$, $-S(O)_nR^7$, nitro, cyano, halogen, $C_6-C_{12}$aryl, substituted $C_6-C_{12}$aryl and protected $-OH$, where $R^6$ is hydrogen or alkyl, n is 0–2 and $R^7$ is hydrogen or alkyl; and c) aryl is cyclic or polycyclic aromatic $C_3-C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6-C_{12}$aryl, alkoxy, acyloxy, substituted $C_6-C_{12}$aryl, amino, N-acylamino, nitro, cyano, halogen, hydroxy, $-C(O)OR^6$, $-S(O)_nR^5$, protected $-OH$ and alkyl substituted with one or more substituents selected from the group consisting of: alkoxy, acyloxy, $C_6-C_{12}$aryl, substituted $C_6-C_{12}$aryl, amino, N-acylamino, oxo, hydroxy, cycloalkyl, substituted cycloalkyl, $-C(O)OR^6$, $-S(O)_nR^7$, aryloxy, nitro, cyano, halogen and protected $-OH$, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; or pharmaceutically acceptable salts, hydrates, solvates and esters thereof.

2. A compound of claim 1 of the Formula

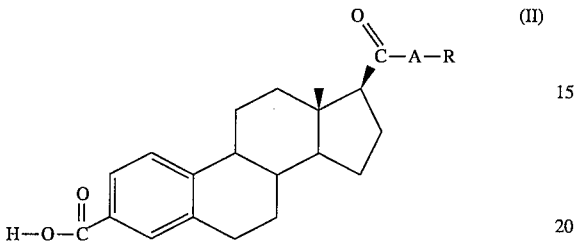

(II)

in which A is absent or present as a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$, where $R^6$ is hydrogen or alkyl, n is 0–2 and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of:

alkoxy, acyloxy, amino, N-acylamino, oxo, hydroxy, cycloalkyl, substituted cycloalkyl, aryloxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl;

b) cycloalkyl is nonaromatic, unsaturated or saturated, cyclic or polycyclic $C_3$–$C_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$,—S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of:

alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and c) aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of:

alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; or pharmaceutically acceptable salts, hydrates, solvates and esters thereof.

3. A compound of claim 2 in which A is absent or present as a linear or branched, saturated or unsaturated hydrocarbon chain containing from 1–6 carbon atoms and R is a) a linear or branched, saturated or unsaturated hydrocarbon chain containing 1–12 carbon atoms substituted with one or more substituents selected from the group consisting of:

—OC$_6$–C$_{12}$aryl, —OC$_1$–C$_4$alkyl, halogen, carboxy and —S(O)$_n$R$^7$, where n is 0–2 and $R^7$ is hydrogen or $C_{1-4}$alkyl;

b) $C_3$–$C_8$ nonaromatic, unsaturated or saturated, cycloalkyl, optionally substituted with one or more substituents selected from the group consisting of: —OC$_6$–C$_{12}$aryl, —(CH$_2$)$_m$OH, —OC$_1$–C$_4$alkyl, $C_6$–$C_{12}$aryl, $C_1$–$C_4$alkyl, trifluoromethyl, halogen, —(CH$_2$)$_p$COOH, —S(O)$_n$R$^7$ and protected —OH, where m is 0–4, p is 0–3, n is 0–2 and $R^7$ is hydrogen or $C_{1-4}$alkyl; or c) $C_4$–$C_{12}$aryl, optionally containing one or more heteroatoms, provided that when C is 4 the aromatic ring contains at least one heteroatom, and optionally substituted with one or more substituents selected from the group consisting of: —OC$_6$–C$_{12}$aryl, —(CH$_2$)$_m$OH, $C_6$–$C_{12}$aryl, $C_1$–$C_4$alkyl,—OC$_1$–C$_4$alkyl, trifluoromethyl, halogen, —(CH$_2$)$_p$COOH, —S(O)$_n$R$^7$ and protected —OH, where m is 0–4, p is 0–3, n is 0–2 and $R^7$ is hydrogen or $C_{1-4}$alkyl; or pharmaceutically acceptable salts, hydrates, solvates and esters thereof.

4. A compound of claim 3 wherein A is absent or present as a linear or branched, saturated or unsaturated hydrocarbon chain containing from 1–4 carbon atoms and R is
   a) $C_3$–$C_8$ nonaromatic, unsaturated or saturated cycloalkyl, optionally substituted with one or more substituents selected from the group consisting of: halogen, thio, methylsulfonyl, methylsulfoxyl, methylthio, carboxy, hydroxy, trifluoromethyl, phenoxy and methoxy or
   b) $C_4$–$C_{12}$aryl, optionally containing one more heteroatoms, provided that when C is 4 the aromatic ring contains at least one heteroatom, and optionally substituted with one or more substituents selected from the group consisting of: halogen, thio, methylsulfonyl, methylsulfoxyl, methylthio, carboxy, hydroxy, trifluoromethyl, phenoxy and methoxy or pharmaceutically acceptable salts, hydrates, solvates and esters thereof.

5. A compound of claim 4 wherein A is absent or present as a linear or branched, saturated or unsaturated hydrocarbon chain containing from 1–4 carbon atoms and R is
   a) $C_5$–$C_7$ cycloalkyl or
   b) $C_4$–$C_{12}$ aryl, optionally containing one or more heteroatoms, provided that when C is 4 the aromatic ring contains at lease one heteroatom, and optionally substituted with one or more substituents selected from the group consisting of: halogen, thio, methylsulfonyl, methylsulfoxyl, methylthio, carboxy, hydroxy, trifluoromethyl, phenoxy and methoxy or pharmaceutically acceptable salts, hydrates, solvates and esters thereof.

6. A compound of claim 5 that is
17β-benzoyl-estra-1,3,5(10)-triene-3-carboxylic acid,
17β-(cyclohexylcarbonyl)-estra-1,3,5-(10)-triene-3-carboxylic acid,
17β-(4-fluorobenzoyl)-estra-1,3,5(10)-triene-3-carboxylic acid,
17β-(benzylcarbonyl)-estra-1,3,5(10)-triene-3-carboxylic acid,
17β-(1-naphthylcarbonyl)-estra-1,3,5(10)-triene-3-carboxylic acid,
17β-(phenethylcarbonyl)-estra-1,3,5(10)-triene-3-carboxylic acid,
17β-(cyclohexylmethylcarbonyl)-estra-1,3,5(10)-triene-3-carboxylic acid,
17β-(cyclohexylethylcarbonyl)-estra-1,3,5(10)-triene-3-carboxylic acid,
17β-(4-biphenylcarbonyl)-estra-1,3,5(10)-triene-3-carboxylic acid,
17β-(3-phenylpropylcarbonyl)-estra-1,3,5(10)-triene-3-carboxylic acid,
17β-(4-methoxybenzoyl)-estra-1,3,5(10)-triene-3-carboxylic acid,
17β-(4-phenoxybenzoyl)-estra-1,3,5(10)-triene-3-carboxylic acid,
17β-(4-trifluoromethylbenzoyl)-estra-1,3,5(10)-triene-3-carboxylic acid,
17β-(4-methylsulfonylbenzoyl)-estra-1,3,5(10)-triene-3-carboxylic acid,
17β-(4-methylthiobenzoyl)-estra-1,3,5(10)-triene-3-carboxylic acid,
17β-(3,5-difluorobenzoyl)-estra-1,3,5(10)-triene-3-carboxylic acid,
17β-(phenylacetylenecarbonyl)-estra-1,3,5(10)-triene-3-carboxylic acid,
17β-(4-methoxyphenethylcarbonyl)-estra-1,3,5(10)-triene-3-carboxylic acid,
17β-(3,4-methylenedioxybenzoyl)-estra-1,3,5(10)-triene-3-carboxylic acid,
17β-(4-hydroxyphenethylcarbonyl)-estra-1,3,5(10)-triene-3-carboxylic acid,
17β-(44-carboxyphenethylcarbonyl)-estra-1,3,5(10)-triene-3-carboxylic acid,
17β-(E-cinnamoyl)-estra-1,3,5(10)-triene-3-carboxylic acid,
17β-(2-furanylcarbonyl)-estra-1,3,5(10)-triene-3-carboxylic acid,
17β-(4-fluorophenethylcarbonyl)-estra-1,3,5(10)-triene-3-carboxylic acid,
17β-(4-methylthiophenethylcarbonyl)-estra-1,3,5(10)-triene-3-carboxylic acid,
17β-(4-methylsulfoxylphenethylcarbonyl)-estra-1,3,5(10)-triene-3-carboxylic acid,
17β-(4-methylsulfonylphenethylcarbonyl)-estra-1,3,5(10)-triene-3-carboxylic acid,
17β-(2-thiophenylcarbonyl)-estra-1,3,5(10)-triene-3-carboxylic acid,
17β-(3-pyridylcarbonyl)-estra-1,3,5(10)-triene-3-carboxylic acid,
17β-(3-pyridylmethylcarbonyl)-estra-1,3,5(10)-triene-3-carboxylic acid,
17β-(4-pyridylmethylcarbonyl)-estra-1,3,5(10)-triene-3-carboxylic acid, or
17β-(2-pyridylethylcarbonyl)-estra-1,3,5(10)-triene-3-carboxylic acid, or pharmaceutically acceptable salts, hydrates, solvates and esters thereof.

7. A compound of claim 1 of the Formula

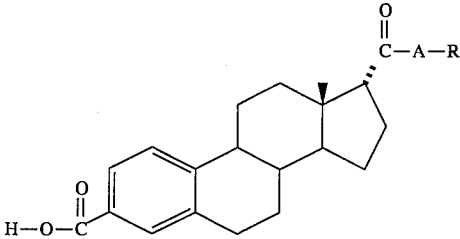

in which A is absent or present as a linear or branched, saturated or unsaturated hydrocarbon chain containing from 1–12 carbon atoms; and
R is substituted alkyl, cycloalkyl or aryl, where
   a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$,
where
   R$^6$ is hydrogen or alkyl,
   n is 0–2 and
   R$^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of:
   alkoxy, acyloxy, amino, N-acylamino, oxo, hydroxy, cycloalkyl, substituted cycloalkyl, aryloxy, —C(O)OR$^6$, —S(O)$_n$R$^7$, nitro, cyano, halogen, $C_6$–$C_{12}$aryl, substituted $C_6$–$C_{12}$aryl and protected —OH, where R$^6$ is hydrogen or alkyl, n is 0–2 and R$^7$ is hydrogen or alkyl;
   b) cycloalkyl is nonaromatic, unsaturated or saturated, cyclic or polycyclic $C_3$–$C_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR⁶, —S(O)ₙR⁵, protected —OH and alkyl substituted with one or more substituents selected from the group consisting of: alkoxy, acyloxy, C₆-C₁₂aryl, substituted C₆-C₁₂aryl, amino, N-acylamino, oxo, hydroxy, cycloalkyl, substituted cycloalkyl, —C(O)OR⁶, —S(O)ₙR⁷, aryloxy, nitro, cyano, halogen and protected —OH, where R⁶ is hydrogen or alkyl, n is 0–2, R⁷ is hydrogen or alkyl and R⁵ is hydrogen, cycloalkyl, C₆-C₁₂aryl, substituted cycloalkyl, substituted C₆-C₁₂aryl, alkyl or alkyl substituted with one or more substituents selected from the group consisting of:

alkoxy, acyloxy, cycloalkyl, substituted cycloalkyl, aryloxy, amino, N-acylamino, oxo, hydroxy, —C(O)OR⁶, —S(O)ₙR⁷, nitro, cyano, halogen, C₆-C₁₂aryl, substituted C₆-C₁₂aryl and protected —OH, where R⁶ is hydrogen or alkyl, n is 0–2 and R⁷ is hydrogen or alkyl; and c) aryl is cyclic or polycyclic aromatic C₃-C₁₂, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, C₆-C₁₂aryl, alkoxy, acyloxy, substituted C₆-C₁₂aryl, amino, N-acylamino, nitro, cyano, halogen, hydroxy, —C(O)OR⁶, —S(O)ₙR⁵, protected —OH and alkyl substituted with one or more substituents selected from the group consisting of: alkoxy, acyloxy, C₆-C₁₂aryl, substituted C₆-C₁₂aryl, amino, N-acylamino, oxo, hydroxy, cycloalkyl, substituted cycloalkyl, —C(O)OR⁶, —S(O)ₙR⁷, aryloxy, nitro, cyano, halogen and protected —OH, where R⁶ is hydrogen or alkyl, n is 0–2, R⁷ is hydrogen or alkyl and R⁵ is hydrogen, cycloalkyl, C₆-C₁₂aryl, substituted cycloalkyl, substituted C₆-C₁₂aryl, alkyl or alkyl substituted with one or more substituents selected from the group consisting of:

alkoxy, acyloxy, aryloxy, amino, N-acylamino, oxo, hydroxy, —C(O)OR⁶, —S(O)ₙR⁷, nitro, cyano, cycloalkyl, substituted cycloalkyl, halogen, C₆-C₁₂aryl, substituted C₆-C₁₂aryl and protected —OH, where R⁶ is hydrogen or alkyl, n is 0–2 and R⁷ is hydrogen or alkyl; or pharmaceutically acceptable salts, hydrates, solvates and esters thereof.

8. A pharmaceutical composition comprising a compound according to claim 1, and a pharmaceutically acceptable carrier.

9. A method of inhibiting steroid 5-α-reductase activity in mammals which comprises administering to a subject in need thereof, an effective therefor amount of a compound according to claim 1.

10. A method or reducing or maintaining prostate size in mammals which comprises administering to a subject in need thereof, an effective therefor amount of a compound according to claim 1.

11. A method of treating prostatic adenocarcinoma in a subject which comprises administering to a subject in need thereof an effective therefor amount of a compound of claim 1.

12. A method of treating baldness in a subject which comprises administering to a subject in need thereof an effective therefor amount of a compound of claim 1.

13. A method of treating acne in a subject that comprises administering to a subject in need thereof an effective therefor amount of a compound of claim 1.

14. A method of treating benign prostatic hypertrophy in a subject that comprises separate sequential or simultaneous administration of a compound according to claim 1 and an alpha-receptor antagonist compound.

15. A method of treating baldness in a subject that comprises separate sequential or simultaneous administration of a compound according to claim 1 and minoxidil.

16. A compound of the formula

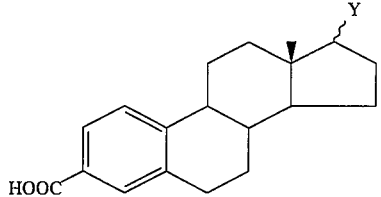

wherein Y is α or β

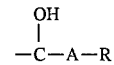

in which A is absent or present as a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR⁶ and —S(O)ₙR⁵, where R⁶ is hydrogen or alkyl, n is 0–2 and R⁵ is hydrogen, cycloalkyl, C₆-C₁₂aryl, substituted cycloalkyl, substituted C₆-C₁₂aryl, alkyl or alkyl substituted with one or more substituents selected from the group consisting of:

alkoxy, acyloxy, amino, N-acylamino, oxo, hydroxy, cycloalkyl, substituted cycloalkyl, aryloxy, —C(O)OR⁶, —S(O)ₙR⁷, nitro, cyano, halogen, C₆-C₁₂aryl, substituted C₆-C₁₂aryl and protected —OH, where R⁶ is hydrogen or alkyl, n is 0–2 and R⁷ is hydrogen or alkyl;

b) cycloalkyl is nonaromatic, unsaturated or saturated, cyclic or polycyclic C₃-C₁₂, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR⁶, —S(O)ₙR⁵, protected —OH and alkyl substituted with one or more substituents selected from the group consisting of: alkoxy, acyloxy, C₆-C₁₂aryl, substituted C₆-C₁₂aryl, amino, N-acylamino, oxo, hydroxy, cycloalkyl, substituted cycloalkyl, —C(O)OR⁶, —S(O)ₙR⁷, aryloxy, nitro, cyano, halogen and protected —OH, where R⁶ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of:

aryloxy, amino, N-acylamino, oxo, hydroxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and c) aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of:

alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; or pharmaceutically acceptable salts, hydrates, solvates and esters thereof.

17. A compound of claim 16 in which Y is in the β position.

18. A compound of claim 16 in which Y is in the α position.

19. A compound of claim 17 in which the compound is 17β-(1-hydroxy-2-phenylethyl)-estra-1,3,5(10)-triene-3-carboxylic acid or 17β-(1-hydroxy-3-phenyl-2-propynyl)-estra-1,3,5(10)-triene-3-carboxylic acid.

20. A process for preparing a compound of the Formula (XI)

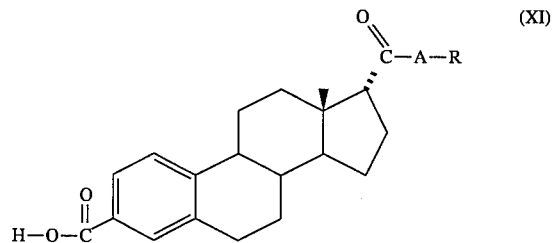

in which A is absent or present as a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$, where $R^6$ is hydrogen or alkyl, n is 0–2 and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of:

alkoxy, acyloxy, amino, N-acylamino, oxo, hydroxy, cycloalkyl, substituted cycloalkyl, aryloxy, —C(O)OR$^6$, —S(O)$_n$R, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl;

b) cycloalkyl is nonaromatic, unsaturated or saturated, cyclic or polycyclic $C_3$–$C_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of:

alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and c) aryl is cyclic or polycyclic aromatic $C_3$–$C_{12}$, optionally containing one or more heteroatoms, provided that when C is 3 the aromatic ting contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of:

alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl; and pharmaceutically acceptable salts, hydrates solvates and esters thereof which comprises epimerization of a compound of Formula (II)

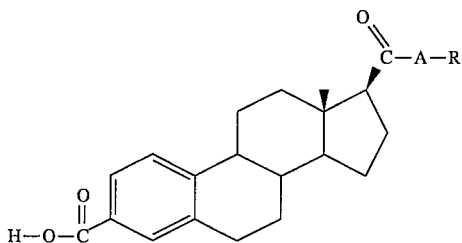

in which A and R are as described above, and thereafter optionally forming a pharmaceutically acceptable salt, hydrate or solvate thereof.

21. A compound of the formula:

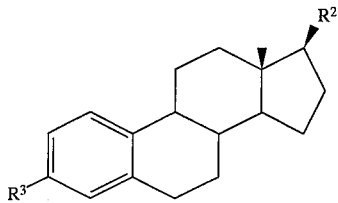

in which

R$^2$ is 2-thiopyridylcarbonyl and

R$^3$ is C$_{1-6}$alkoxycarbonyl, trifluoromethylsulfonyloxy, hydroxy or fluorosulfonyloxy.

22. A compound of the formula:

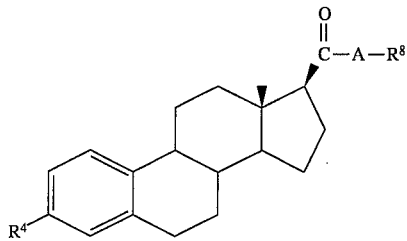

in which A is absent or present as a linear or branched, saturated or unsaturated hydrocarbon chain containing from 1–12 carbon atoms; and R$^8$ is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$, where R$^6$ is hydrogen or alkyl, n is 0–2 and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of:

alkoxy, acyloxy, aryloxy, amino, N-acylamino, oxo, hydroxy, cycloalkyl, substituted cycloalkyl, aryloxy, —C(O)OR$^6$, —S(O)$_n$R$^7$, nitro, cyano, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl;

b) cycloalkyl is nonaromatic, unsaturated or saturated, cyclic or polycyclic C$_3$–C$_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of: alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where R$^6$ is hydrogen or alkyl, n is 0–2, R$^7$ is hydrogen or alkyl and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of:

alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl; and c) aryl is cyclic or polycyclic aromatic C$_3$–C$_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, C$_6$–C$_{12}$aryl, alkoxy, acyloxy, substituted C$_6$–C$_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where R$^6$ is hydrogen or alkyl, n is 0–2, R$^7$ is hydrogen or alkyl and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of:

alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl; or moieties which can be chemically convened into moieties a, b or c; and R$^4$ is trifluoromethylsulfonyloxy, fluorosulfonyloxy or hydroxy.

23. A compound of the Formula (VI)

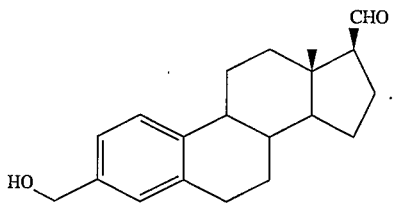

24. A compound of the Formula (VII)

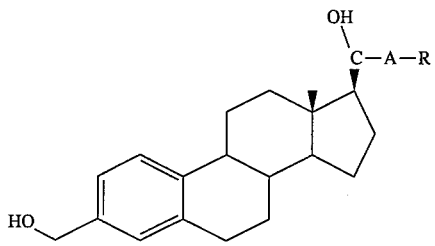

in which A is absent or present as a linear or branched, saturated or unsaturated hydrocarbon chain containing from 1–12 carbon atoms; and
R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$, where R$^6$ is hydrogen or alkyl, n is 0–2 and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of:

alkoxy, acyloxy, amino, N-acylamino, oxo, hydroxy, cycloalkyl, substituted cycloalkyl, aryloxy, —C(O)OR$^6$, —S(O)$_n$R$^7$, nitro, cyano, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl;

b) cycloalkyl is nonaromatic, unsaturated or saturated, cyclic or polycyclic C$_3$–C$_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of: alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where R$^6$ is hydrogen or alkyl, n is 0–2, R$^7$ is hydrogen or alkyl and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of:

alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl; and c) aryl is cyclic or polycyclic aromatic C$_3$–C$_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, C$_6$–C$_{12}$aryl, alkoxy, acyloxy, substituted C$_6$–C$_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where R$^6$ is hydrogen or alkyl, n is 0–2, R$^7$ is hydrogen or alkyl and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of:

alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl.

* * * * *